US012625141B2

(12) United States Patent
Zhu et al.

(10) Patent No.: US 12,625,141 B2
(45) Date of Patent: May 12, 2026

(54) FLUORESCENT DYE, PREPARATION METHOD AND USES THEREOF

(71) Applicant: FLUORESCENCE DIAGNOSIS (SHANGHAI) BIOTECH COMPANY LTD., Shanghai (CN)

(72) Inventors: Linyong Zhu, Shanghai (CN); Yi Yang, Shanghai (CN); Dasheng Zhang, Shanghai (CN); Xianjun Chen, Shanghai (CN); Qiuning Lin, Shanghai (CN); Ni Su, Shanghai (CN)

(73) Assignee: FLUORESCENCE DIAGNOSIS (SHANGHAI) BIOTECH COMPANY LTD, Shanghai (CN)

( * ) Notice: Subject to any disclaimer, the term of this patent is extended or adjusted under 35 U.S.C. 154(b) by 1143 days.

(21) Appl. No.: 17/607,005

(22) PCT Filed: Apr. 27, 2020

(86) PCT No.: PCT/CN2020/087311

§ 371 (c)(1),
(2) Date: Oct. 27, 2021

(87) PCT Pub. No.: WO2020/221217

PCT Pub. Date: Nov. 5, 2020

(65) Prior Publication Data

US 2022/0214351 A1 Jul. 7, 2022

(30) Foreign Application Priority Data

Apr. 28, 2019 (CN) ........................ 201910352348.X

(51) Int. Cl.

| | |
|---|---|
| ***G01N 33/533*** | (2006.01) |
| ***C09B 1/00*** | (2006.01) |
| ***C09B 23/10*** | (2006.01) |
| ***C09B 23/14*** | (2006.01) |
| ***C09B 57/00*** | (2006.01) |
| ***C09K 11/06*** | (2006.01) |
| ***G01N 33/58*** | (2006.01) |

(52) U.S. Cl.

CPC ............. *G01N 33/582* (2013.01); *C09B 1/00* (2013.01); *C09B 23/105* (2013.01); *C09B 23/143* (2013.01); *C09B 23/145* (2013.01); *C09B 23/148* (2013.01); *C09B 57/00* (2013.01); *C09K 11/06* (2013.01); *G01N 33/533* (2013.01); *C09K 2211/1022* (2013.01); *C09K 2211/1033* (2013.01); *C09K 2211/1044* (2013.01); *C09K 2211/1092* (2013.01); *C09K 2211/1096* (2013.01)

(58) Field of Classification Search

CPC ...... G01N 33/582; G01N 33/533; C09B 1/00; C09B 23/105; C09B 23/143; C09B 23/145; C09B 23/148; C09B 57/00; C09K 11/06

USPC ........................................................ 436/172

See application file for complete search history.

(56) References Cited

U.S. PATENT DOCUMENTS

| | | | | |
|---|---|---|---|---|
| 4,016,195 | A * | 4/1977 | Pintschovius | D06L 4/657 562/490 |
| 5,387,487 | A * | 2/1995 | Shoshi | C07C 255/34 430/58.35 |
| 5,589,506 | A | 12/1996 | Hashimoto et al. | |
| 6,335,446 | B1 | 1/2002 | Pennington et al. | |
| 2004/0047806 | A1 | 3/2004 | Theodoropulos | |

FOREIGN PATENT DOCUMENTS

| | | | |
|---|---|---|---|
| CN | 102399169 | A | 4/2012 |
| CN | 106939163 | A | 7/2017 |
| CN | 107641121 | A | 1/2018 |
| CN | 107663384 | A | 2/2018 |
| CN | 109574880 | A | 4/2019 |
| JP | 06027507 | A * | 2/1994 |
| JP | 06059473 | A * | 3/1994 |
| JP | 2004262888 | A | 9/2004 |

OTHER PUBLICATIONS

Ji, L. et al, SPIE 2005, 5646, 67-72. (Year: 2005).*
Huang, G.-J. et al, Chemistry and Asian Journal 2010, 5, 2075-2085. (Year: 2010).*
Palakollu, Palakollu et al, New Journal of Chemistry 2014, 38, 5736-5746. (Year: 2014).*
Chen, X. et al, Nature Biotechnology 2019, 37, 1287-1293 with 46 pages of supplementary information. (Year: 2019).*
Lu, Z. et al, Angewandte Chemie International Edition 2020, 59, 4299-4303. (Year: 2020).*
Il'ichev, Y. V. et al., Berichte der Bunsen-Gesellschaft für Physikalische Chemie 1997, 101, 625-635. (Year: 1997).*
Dubey, P.K. et al., Arkivoc 2007, 15, 192-198. (Year: 2007).*
An, B.-K. et al, Journal of the American Chemical Society 2009, 131, 3950-3957 with 18 pages of supporting information (Year: 2009).*
Zhu, L.-L. et al, Langmuir 2009, 25, 3482-3486 with 13 pages of supporting information. (Year: 2009).*

(Continued)

*Primary Examiner* — Arlen Soderquist

(74) *Attorney, Agent, or Firm* — HAUPTMAN HAM, LLP

(57) ABSTRACT

A fluorescent dye, as well as a preparation method and uses thereof, wherein the fluorescent dye is sensitive and specific to viscosity and has low background fluorescence; it can also be used as a fluorescent activated and lighted probe used for fluorescent labeling, quantification or monitoring of protein, enzymes or nucleic acid.

5 Claims, 3 Drawing Sheets

Specification includes a Sequence Listing.

(56) References Cited

OTHER PUBLICATIONS

Chung, J. W. et al, Journal of Materials Chemistry 2009, 19, 5920-5925. (Year: 2009).*
Chung, J. W. et al, Journal of Materials Chemistry 2010, 20, 7715-7720. (Year: 2010).*
Makowski, B. T. et al, Journal of Materials Chemistry 2012, 22, 5190-5196. (Year: 2012).*
Chung, J. W. et al, Journal of Physical Chemistry C 2013, 117, 11285-11291 with 5 pages of.supporting information. (Year: 2013).*
Wang, C.-C. et al, Chinese Chemical Letters 2015, 26, 323-328. (Year: 2015).*
Jin, Y. et al, Soft Matter 2015, 11, 798-805. (Year: 2015).*
Mandal, A. K. et al, ACS Nano 2015, 9, 4796-4805 with 47 pages of supporting information. (Year: 2015).*
Ramesh, N. et al, Journal of Physical Chemistry C 2016, 120, 1909-1917. (Year: 2016).*
Paramasivam, M. et al, Journal of Physical Chemistry C 2016, 120, 10757-10769. (Year: 2016).*
Zhou, Y. et al, Chemistry A European Journal 2017, 23, 7642-7647 with 18 pages of supporting information. (Year: 2017).*
Mahesh, K. et al, Journal of Molecular Structure 2018, 1154, 445-454. (Year: 2018).*
Agarwal, D. S. et al, Molecular Diversity 2018, 22, 305-321. (Year: 2018).*
Simalou, O. et al, Comptes Rendus Chimie 2018, 21, 88-96. (Year: 2018).*
Zhou, Y. et al, Journal of Physical Chemistry Letters 2018, 9, 550-556 with 26 pages of supporting information. (Year: 2018).*
Redon, S. et al, Dyes and Pigments 2018, 156, 116-132. (Year: 2018).*
Yokoyama, S. et al, Journal of Organic Chemistry 2019, 84, 1192-1200. (Year: 2019).*
Suntsova, P. O. et al, Dyes and Pigments 2019, 166, 60-71. (Year: 2019).*
Niu, G. et al, Journal of the American Chemical Society 2019, 141, 15111-15120 with 19 pages of supporting information. (Year: 2019).*
Katla, J. et al, Chem PlusChem 2019, 84, 1789-1795 with 15 pages of supporting information. (Year: 2019).*
Jana, P. et al, New Journal of Chemistry 2020, 44, 218-230 with 14 pages of supplementary material. (Year: 2020).*
Fields, E. K., Journal of the American Chemical Society 1949, 71, 1495-1496. (Year: 1949).*
Castle, R. N. et al., Journal of Organic Chemistry 1955, 20, 987-989. (Year: 1955).*
Ichimura, K., Heterogeneous Chemistry Reviews 1996, 3, 419-441. (Year: 1996).*
Carta, A. et al., Heterocycles 2002, 57, 1079-1090. (Year: 2002).*
Saczewski, F. et al, European Journal of Medicinal Chemistry 2008, 43, 1847-1857. (Year: 2008).*
Percino, M. J., et al, Chemical Papers 2010, 64, 360-367. (Year: 2010).*
Percino, M. J., et al, Chemical Papers 2011, 65, 42-51. (Year: 2011).*
Perez-Gutierrez, E. et al, Materials 2011, 4, 562-574. (Year: 2011).*
Ma, J. et al, Bioorganic & Medicinal Chemistry Letters 2017 27, 81-85. (Year: 2017).*
Alneyadi, S. S. et al, European Journal of Medicinal Chemistry 2017, 136, 270-28/2. (Year: 2017).*
Arun, Kalliat T. et al.; Near-Infrared Fluorescent Probes: Synthesis and Spectroscopic Investigations of a Few Amphiphilic Squaraine Dyes; J. Phys. Chem. A. 2005, 109, pp. 5571-5578.
Chen, Xianjun et al.; Visualizing RNA dynamics in live cells with bright and stable fluorescent RNAs; Nature Biotechnology, vol. 37 No. 11, Nov. 23, 2019; pp. 1287-1293.
Lu, Zhuoqun et al.; Optical Waveguiding Organic Single Crystals Exhibiting Physical and Chemical Bending Features; Angewandte Chemie International Edition, vol. 59 No. 11, Jan. 29, 2020; pp. 4299-4303.
Lim, Chang-keun et al.; Dye-Condensed Biopolymeric Hybrids: Chromophoric Aggregation and Self-Assembly toward Fluorescent Bionanoparticles for Near Infrared Bioimaging; Chemistry of Materials, vol. 21 No. 24, Nov. 24, 2009; pp. 5819-5825.
Kaumanns, Oliver et al.; Nucleophilicities of the Anions of Arylacetonitriles and Arylpropionitriles in Dimethyl Sulfoxide; Journal of Organic Chemistry, vol. 74 No. 1, Nov. 26, 2008; pp. 75-81.
S'Heeren, G. et al.; Synthesis of Frequency Doubling Nonlinear Optical Polymers, Functionalized With Aminocyano- and Alkoxycyano-Stilbene Dyes. Second Harmoic Generation in Corona Poled Thin Films; European Polymer Journal, vol. 30 No. 7, Jul. 31, 1994; pp. 775-779.
Gierschner, Johannes et. al.; Preparation and Optical Properties of Oligophenylenevinylene/Perhydrotriphenyle Inclusion Compounds, vol. 12, No. 10, Feb. 29, 2000; pp. 757-761.
Mustroph, H. et. al.; UV/VIS Spectral Behavior of Azo Dyes. IX. The Absorption Behavior of Azo Dyes of 4'-Diethylamino-a-Cyanostillbene-4-Diazonium Ions; Journal fuer Signalaufzeichnungs Materialien, vol. 12 No. 2, Dec. 31, 1984; pp. 115-120 (with English Summary).
Binev I. G. et al.; Nitrile Frequency and Intensity-Structure Relationships of Trans-1,2-Diaryl-Agrylonitriles/L. F. E. R. and Quantum-Chemical Approaches, Izcestiya po Khimiya, vol. 12, No. 2, Dec. 31, 1979; pp. 228-246.
Binev I. G. et al.; Infrared Spectra and Structure of Carbanions. XII. Dimeric Dianions Derived from α, β-Diarylacrylonitriles; Journal of Organometallic Chemistry, vol. 141, No. 2, Dec. 31, 1977; pp. 123-131.
Binev I. G. et al.; Infrared Spectra and Structure of Carbanions. V. Carbanions-Intermediates in Nucleophillic Addition Recations to α, β-Diaryl-Cyanoethylenes; Izcestiya po Khimiya, vol. 9 No. 1, Dec. 31, 1976; pp. 33-51.
Es van, T. et. al.; Some Sulphonamido-Derivatives of Stilbene and Acetophenone, Journal of the South African Chemical Institute, vol. 17 No.2, Dec. 31, 1964; pp. 95-100.
Pfeiffer, P., et al.; Theory of the Betaines.III; Justus Liebigs Annalen der Chemie, vol. 465, Dec. 31, 1928; pp. 20-51.
International Search Report and Written Opinion issued in International Application No. PCT/CN2020/087311; mailed Jul. 20, 2020; 29 pgs.
Office Action issued in corresponding Chinese Application No. 201910352348.X; mailed Mar. 31, 2021; 34 pgs.
Second Office Action and Supplementary Search issued in corresponding Chinese Application No. 201910352348.X; mailed Feb. 11, 2022; 16 pages.
First Notice of Reasons for Rejection issued in Corresponding Japanese Application 2021-564230; mailed Dec. 6, 2022; 7 pages.
Second Notice of Reasons for Rejection issued in Corresponding Japanese Application 2021-564230; mailed Mar. 22, 2023; 3 pages.
Supplementary Search Report in corresponding European Application No. 20798794.2; mailed Dec. 11, 2023; 15 pages.
Manohara, Subbaiah et al; Cyanovinyl substituted benzimidazole based (D-pi-A) organic dyes for fabrication of dye sensitized solar cells; Dyes and Pigments, vol. 105; 2014, pp. 223-231.

* cited by examiner

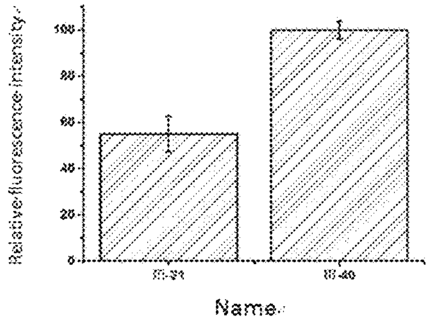
Fig. 13
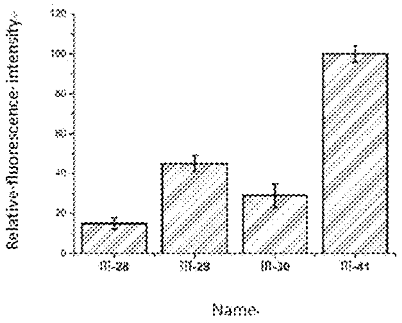
Fig.14
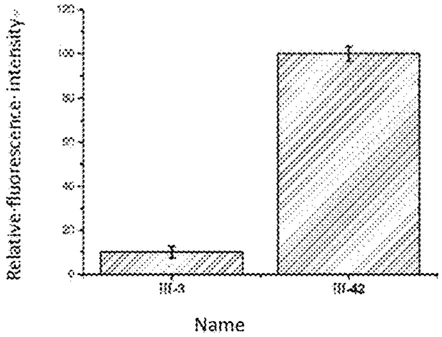
Fig. 15
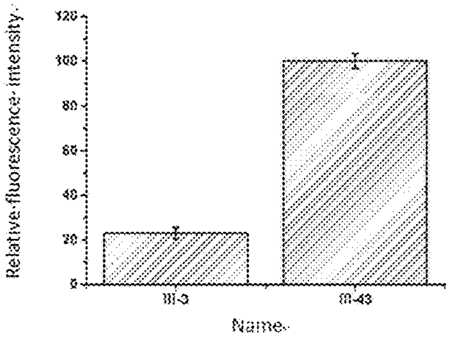
Fig.16
Fig. 17 A
Fig. 17 B
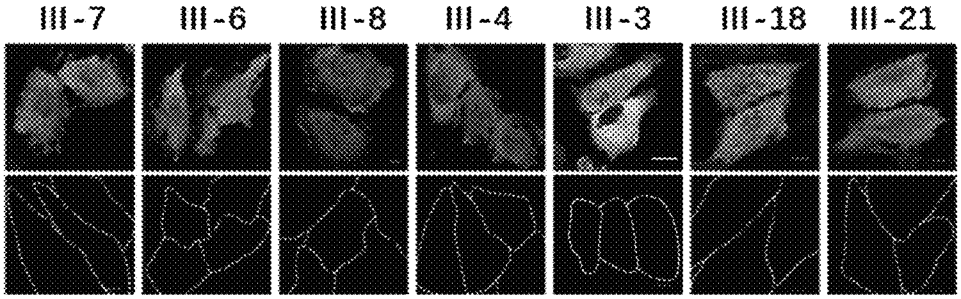
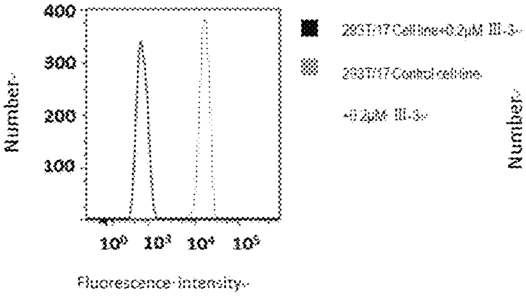
Fig. 18A
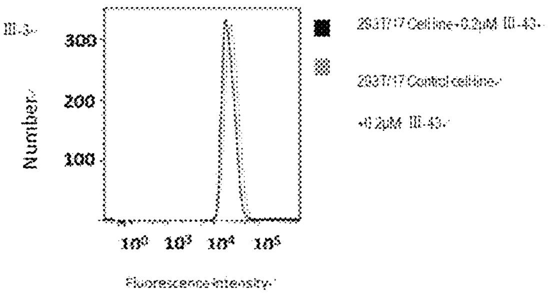
Fig. 18B

FLUORESCENT DYE, PREPARATION METHOD AND USES THEREOF

RELATED APPLICATIONS

The present application is a U.S. National Phase of International Application Number PCT/CN2020087311 filed Apr. 27, 2020 and claims priority to Chinese Application Number CN 201910352348.X filed Apr. 28, 2019.

INCORPORATION BY REFERENCE

The sequence listing provided in the file entitled 072-2110093US-SEQUENCE LISTING_revised_27.10.2021.txt, which is an ASCII text file that was created on Oct. 27, 2021, and which comprises 2,896 bytes, is hereby incorporated by reference in its entirety.

TECHNICAL FIELD

The present invention relates to the technical field of fluorescent dye, and particularly relates to a fluorescent dye with viscosity responsiveness and low background fluorescence, as well as a preparation method and uses thereof.

BACKGROUND

Molecular rotors are a kind of dyes the fluorescence intensity of which changes with microenvironment viscosity. After excitation of molecular rotors, conformation of molecules is twisted and TICT (twisted intramolecular charge transfer) is formed, wherein the excited energy are mainly released in a non-radiative form; when the molecules are in a microenvironment of comparatively large viscosity or rigidity, the twisted molecular conformation will be restricted for this kind of molecules, and the excited energy of dye will be mainly released in the form of radioluminescence, namely, the fluorescence property of molecules is activated. It is important that the fluorescence intensity of this kind of molecules changes with the microenvironment viscosity, so that the viscosity change of the microenvironment is displayed in real time, in situ and in a sensitive and visual manner.

At present, besides the field of viscosity detection, the twisted conformation based on restrictions of the molecular rotors is also widely used for constructing a fluorescent activated probe, for example, after the combination of molecular rotors with BSA, the conformation of molecules is restricted by protein, and the fluorescence is lit up, but the excited energy of the dye that is not combined with protein is still dissipated in a non-radiative form, thereby detecting and quantifying the protein in real time. For another example, Thiazole Orange is in a state of fluorescence quenching before it is combined with DNA or RNA, and the molecular conformation is restricted after it is combined with DNA or RNA, as a result of which the fluorescence is activated, so Thiazole Orange is widely used for the detection and tracing of DNA and RNA; molecular rotors such as Malachite Green are coated with antibodies so as to limit the conformation changes of the molecules and are used for protein-activated fluorescence imaging; DHBI is combined with an adapter so as to construct fluorescent protein simulators for RNA tracing; for another example, the combination with amyloid protein can restrict the conformation changes of molecules, and can be used for the detection, research and so on of Alzheimer's disease.

However, current molecular rotors generally have the disadvantage of high fluorescence background, namely, the fluorescent intensity of molecular rotors in a free state is comparatively high, and thus can hardly be used for the sample detection and labeling with a small sample size, complicated components and low abundance of objects to be measured, such as endogenous proteins, nucleic acid, metabolites and so on in biological samples, so the development of a kind of molecular rotors with low background fluorescence can further expand the use of current molecular rotors.

SUMMARY OF THE INVENTION

The object of the present invention is to provide a fluorescent dye with viscosity responsiveness and low background fluorescence.

For one aspect, the present invention provides a fluorescent dye, wherein the fluorescent dye is shown as Formula (I), (I)

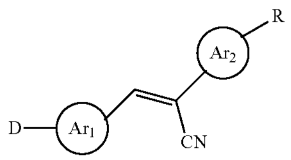

wherein:

D- is HO— or $N(X_1)(X_2)$—, $X_1$ and $X_2$ are respectively and independently selected from hydrogen, alkyl and modified alkyl; and $X_1$ and $X_2$ are optionally interconnected, and form a lipid heterocyclic ring with N atoms;

R is selected from cyano group, carboxy, amide group, ester group, sulfoxide group, sulphone group, sulfonic ester group or sulfonamido group; $Ar_1$ and $Ar_2$ are respectively and independently selected from arylene and sub-heteroaryl; wherein hydrogen atoms in $Ar_1$ and $Ar_2$ being optionally, respectively and independently substituted by halogen atoms, hydroxyl group, aldehyde group, carboxyl group, ester group, amide group, cyano group, sulfonic acid group, phosphoric acid group, amino group, primary amino group, secondary amino group, alkyl or modified alkyl;

$X_1$ and $X_2$ optionally and independently form a lipid heterocyclic ring with $Ar_1$;

wherein: the "alkyl" is respectively and independently C-Cia straight or branched alkyl; optionally, the "alkyl group" is $C_1$-$C_7$ straight or branched alkyl; optionally, the "alkyl group" is $C_1$-$C_5$ straight or branched alkyl; optionally, the "alkyl group" is selected from methyl, ethyl, n-propyl, isopropyl, n-butyl, isobutyl, tertiary butyl, sec-butyl, n-amyl, 1-methyl butyl, 2-methyl butyl, 3-methyl butyl, isoamyl, 1-ethyl propyl, neoamyl, n-hexyl, 1-methyl amyl, 2-methyl amyl, 3-methyl amyl, isohexyl, 1,1-dimethyl butyl, 2,2-dimethyl butyl, 3,3-dimethyl butyl, 1,2-dimethyl butyl, 1,3-dimethyl butyl, 2,3-dimethyl butyl, 2-ethyl butyl, n-heptyl, 2-methyl hexyl, 3-methyl hexyl, 2,2-dimethyl amyl, 3,3 dimethyl amyl, 2,3-dimethyl amyl, 2,4-dimethyl amyl, 3-ethyl amyl or 2,2,3-methyl butyl;

the "modified alkyl" is respectively and independently a group obtained by replacing any carbon atom in alkyl with one or more groups of halogen atom, —OH, —CO—, —O—, —CN, —S—, —$SO_2$—, —(S═O)—, azido, primary amino group, secondary amino group, tertiary amino group, and quaternary ammonium base, and the modified alkyl has 1-10 carbon atoms, wherein the carbon-carbon single bond is optionally and independently replaced by a carbon-carbon double bond or a carbon-carbon triple bond;

the replacement of carbon atoms refers to that carbon atoms or the carbon atoms and hydrogen atoms thereon together are replaced by a corresponding group;

the "halogen atom" is respectively and independently F, Cl, Br or I;

the "lipid heterocyclic ring" is a saturated or unsaturated 4- to 15-membered monocyclic or polycyclic lipid heterocyclic ring containing one or more heteroatoms of N, O, S or Si on the ring, and the lipid heterocyclic ring is —S—, —SO— or —$SO_2$— when there are S atoms on the ring; the lipid heterocyclic ring is optionally substituted by a halogen atom, an alkyl, an aryl or a modified alkyl;

the "arylene" is a 5- to 13-membered monocyclic or dicyclic or fused dicyclic or fused polycyclic subaromatic group;

the "sub-heteroaryl" is a 5- to 13-membered monocyclic or dicyclic or fused dicyclic or fused polycyclic sub-heteroaromatic group containing one or more heteroatoms of N, O, S or Si on the ring;

the "ester group" is R'(C═O)OR" group;

the "amide group" is R'CONR"R" group;

the "sulfonic acid group" is $R'SO_3H$ group;

the "sulfonic ester group" is $R'SO_2OR''$ group;

the "sulfonamido group" is $R'SO_2NR''R'''$ group;

the "phosphoric acid group" is $R'OP({=}O)(OH)_2$ group;

the "sulphone group" is $R'SO_2R''$ group;

the "sulfoxide group" is R'SOR" group;

the "primary amino group" is $R'NH_2$ group;

the "secondary amino group" is R'NHR" group;

the "tertiary amino group" is R'NR"R'" group;

the "quaternary ammonium base" is $R'R''R'''R''''N^+$ group;

each R', R", R'", R"" respectively and independently being single bond, hydrogen, alkyl, alkylene, modified alkyl or modified alkylene;

the "alkylene" is $C_1$-$C_{10}$ straight or branched alkylene; optionally, it is $C_1$-$C_7$ straight or branched alkylene; optionally, it is $C_1$-$C_5$ straight or branched alkylene;

the "modified alkylene" is a group obtained by replacing any carbon atom in $C_1$-$C_{10}$ (preferably $C_1$-$C_6$) alkylene with a group selected from —O—, —OH, —CO—, —CS—, and —(S═O)—;

optionally, the "modified alkylene" is a group containing one or more groups selected from —OH, —O—, ethylene glycol unit (—$(CH_2CH_2O)_n$—), monosaccharide unit, —O—CO—, —NH—CO—, —$SO_2$—O—, —SO—, $Me_2N$—, $Et_2N$—, —S—S—, —CH═CH—, F, Cl, Br, I, cyano group; and optionally, $Ar_1$ and $Ar_2$ respectively and independently are structures selected from the following Formulae (II-1) to (II-22):

(II-1)

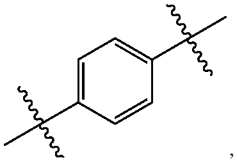

,

-continued (II-2)

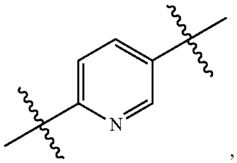

, (II-3)

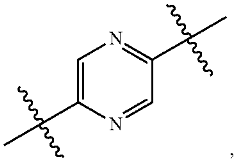

, (II-4)

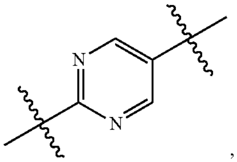

, (II-5)

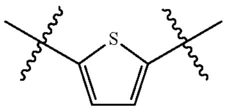

, (II-6)

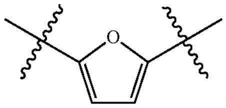

, (II-7)

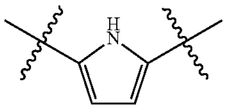

, (II-8)

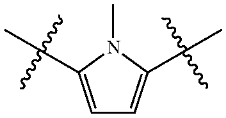

, (II-9)

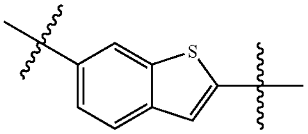

, (II-10)

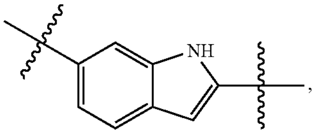

, (II-11)

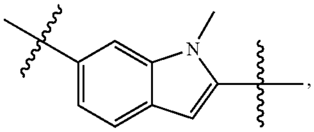

, (II-12)

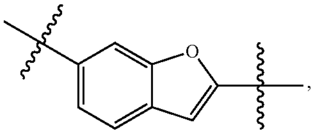

,

-continued
(II-13)
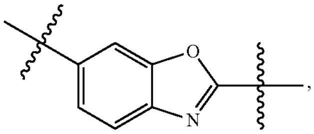
(II-14)
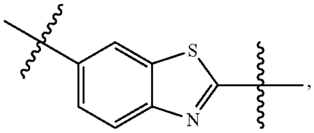
(II-15)
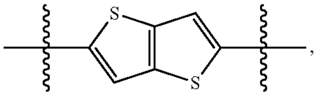
(II-16)
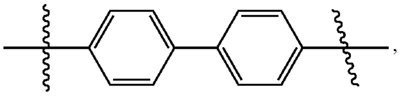
(II-17)
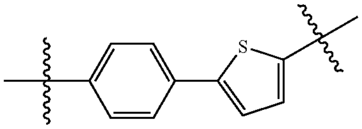
,
(II-18)
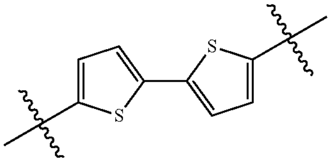
,
(II-19)
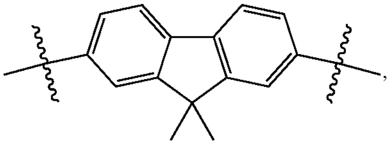
(II-20)
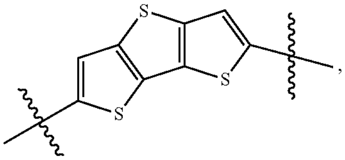
(II-21)
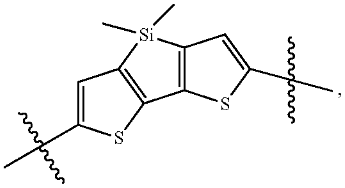
(II-22)
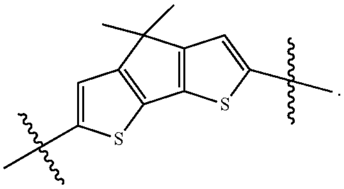
Optionally, the compound represented by Formula (I) is selected from the compounds below:
III-1
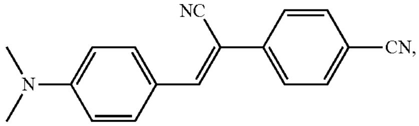
III-2
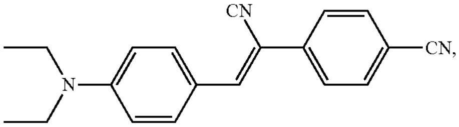
III-3
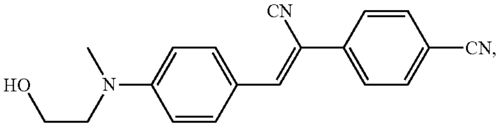
III-4
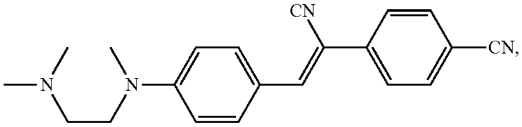
III-5
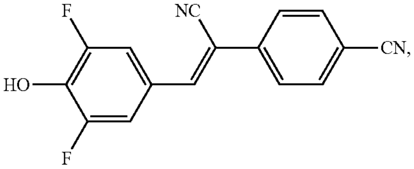
III-6
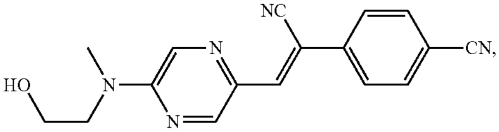
III-7
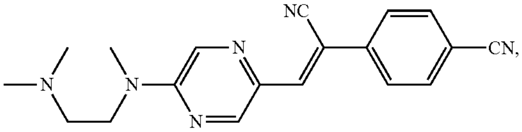
III-8
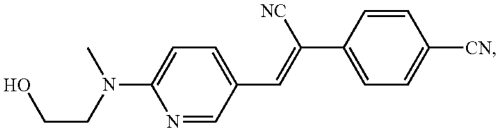
III-9
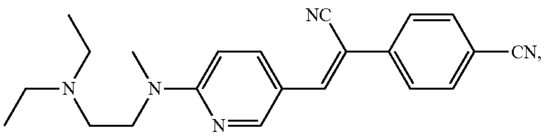
III-10
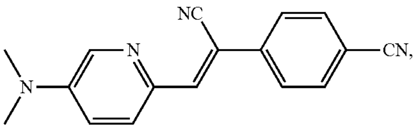

-continued
III-11
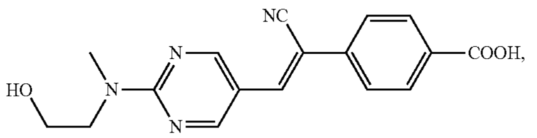
III-12
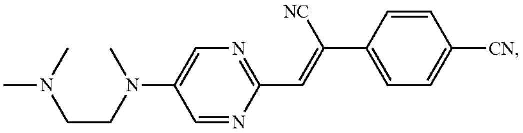
III-13
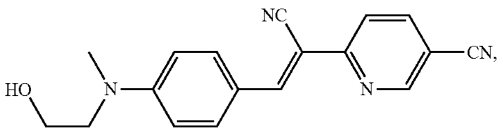
III-14
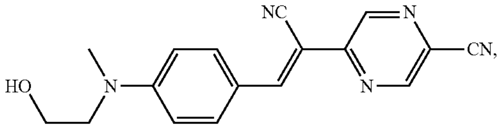
III-15
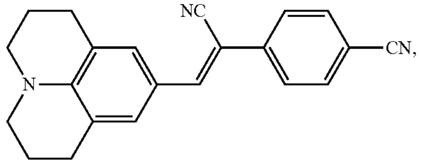
III-16
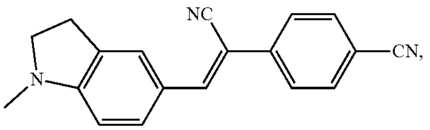
III-17
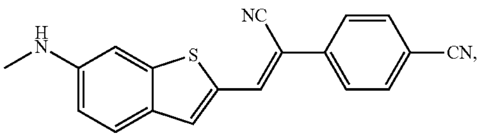
III-18
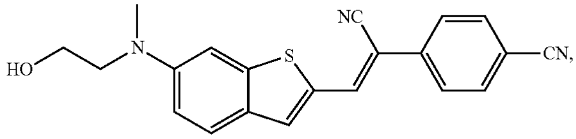
III-19
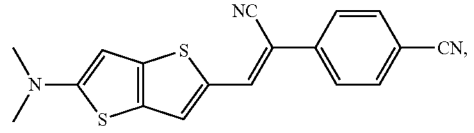
III-20
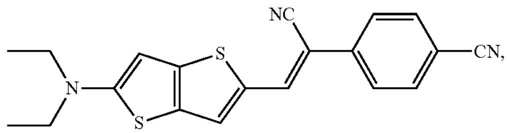
-continued
III-21
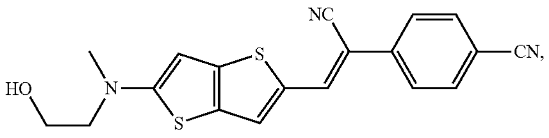
III-22
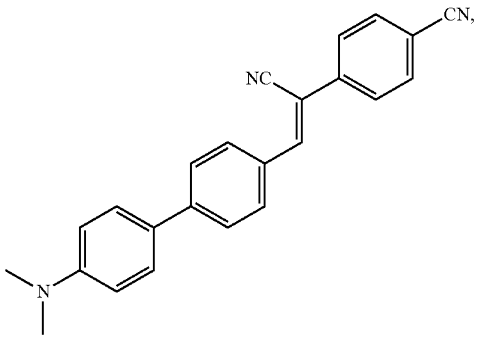
III-23
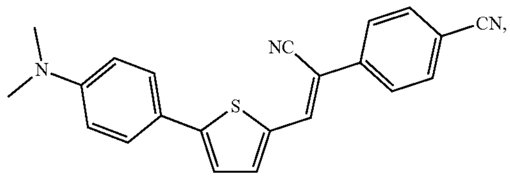
III-24
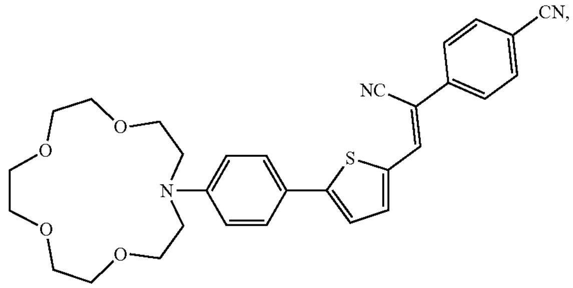
III-25
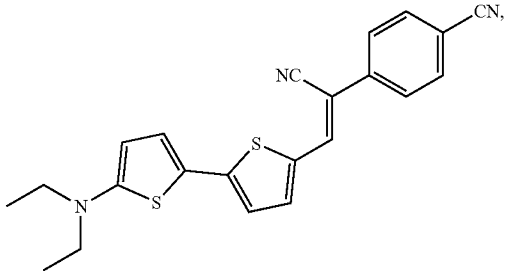
III-26
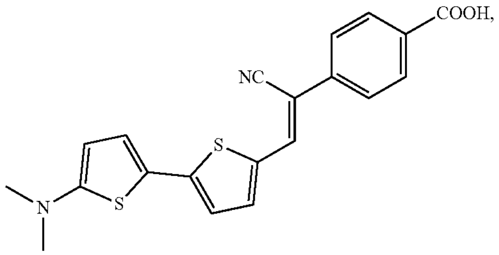

-continued

III-27

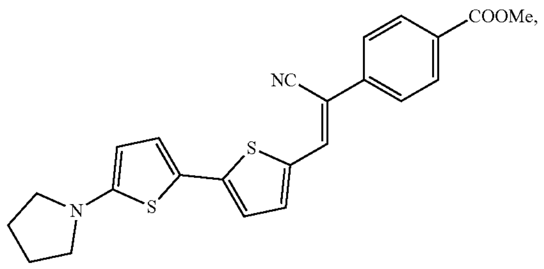

III-28

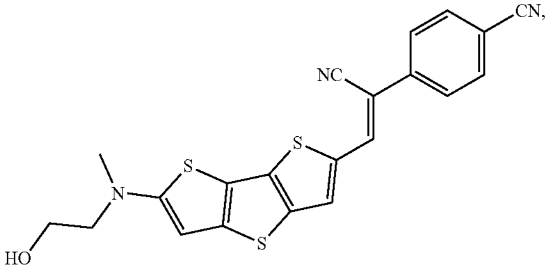

III-29

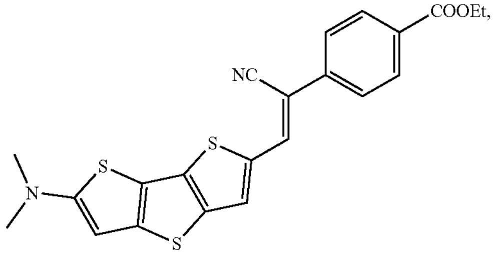

III-30

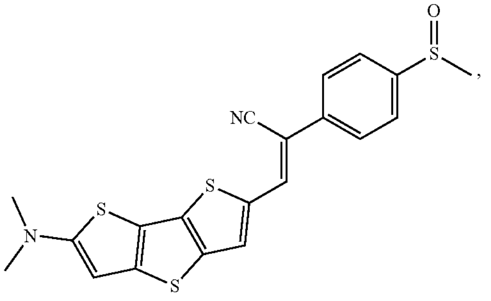

III-31

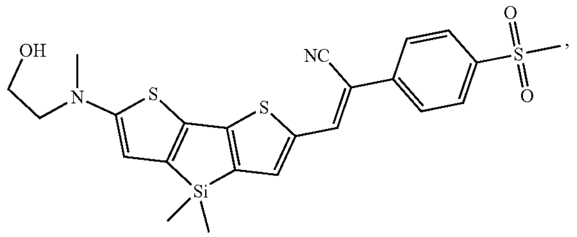

-continued

III-32

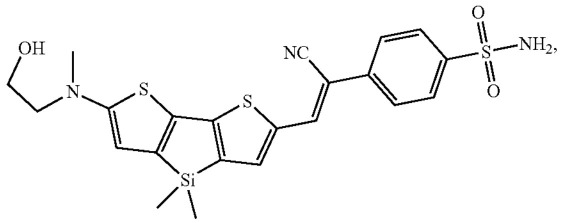

III-33

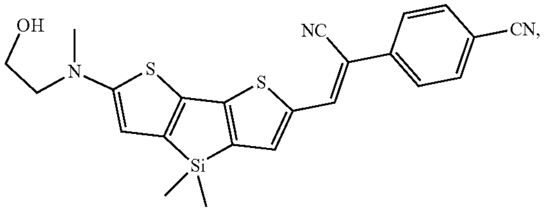

III-34

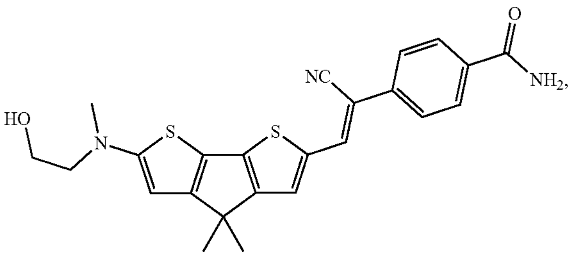

III-35

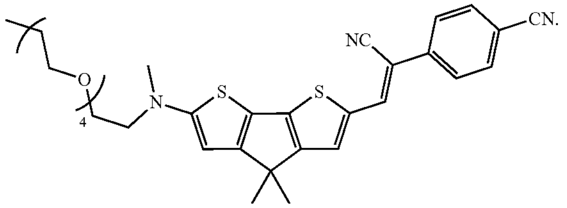

A second aspect of the present invention is to provide a method of preparing the afore-mentioned fluorescent dye, including a step of aldol condensation reaction between a compound of Formula (a) and a compound of Formula (b).

(a)

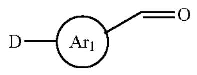

(b)

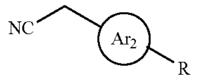

A third aspect of the present invention is to provide uses of the afore-mentioned fluorescent dye in viscosity testing, protein fluorescent labeling, nucleic acid fluorescent labeling, protein quantification or detection, or nucleic acid quantification or detection, wherein the uses are those other than for diagnostic methods of diseases.

A fourth aspect of the present invention is to provide uses of the afore-mentioned fluorescent dye in preparing reagents for viscosity testing, protein fluorescent labeling, nucleic acid fluorescent labeling, protein quantification or detection, or nucleic acid quantification or detection.

A fifth aspect of the present invention is to provide a fluorescent activated and lighted probe, comprising the afore-mentioned fluorescent dye.

A sixth aspect of the present invention is to provide uses of the afore-mentioned fluorescent activated and lighted probe in protein fluorescent labeling, nucleic acid fluorescent labeling, protein quantification or detection, or nucleic acid quantification or detection, wherein the uses are those other than for diagnostic methods of diseases.

A seventh aspect of the present invention is to provide uses of the afore-mentioned fluorescent activated and lighted probe in preparing reagents for protein fluorescent labeling, nucleic acid fluorescent labeling, protein quantification or detection, or nucleic acid quantification or detection.

The fluorescent dye of the present invention can be used for measuring viscosity of samples, such as for the tests of micro-viscosity. According to the embodiments of another aspect, the obtained fluorescent dye can be specifically combined with corresponding antibody, aptamer or amyloid, or bound to the protein tag or enzyme via a ligand or inhibitor, thereby obtaining a series of fluorescent activated and lighted probes used for fluorescent labeling, quantification or monitoring of protein, enzymes or nucleic acids.

DESCRIPTION OF DRAWINGS

FIG. 13 is a diagram showing the fluorescence background contrast of molecular rotors III-21 and III-40 ($1\times10^{-6}$ M) in PBS;

FIG. 14 is a diagram showing the fluorescence background contrast of molecular rotors III-28, III-29, III-30 and III-41 ($1\times10^{-6}$ M) in PBS;

FIG. 15 is a diagram showing the fluorescence background contrast of molecular rotors III-3 and III-42 ($1\times10^{-6}$ M) in PBS;

FIG. 16 is a diagram showing the fluorescence background contrast of molecular rotors III-3 and III-43 ($1\times10^{-6}$ M) in PBS;

FIGS. 17A and 17B are the application of molecular rotors III-3, III-4, III-6, III-7, III-8, III-18, III-21 in labeling intracellular RNA aptamers, wherein A are cells expressing the target RNA aptamers, and B are cells not expressing the target RNA aptamers;

FIGS. 18A and 18B are the application of molecular rotors III-3, III-43 in labeling intracellular mRNA.

SPECIFIC IMPLEMENTATION

Compound III-1

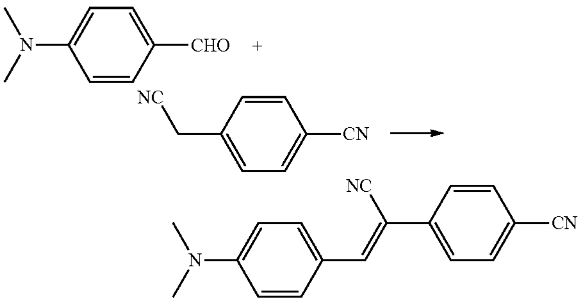

III-1

Figure 1:
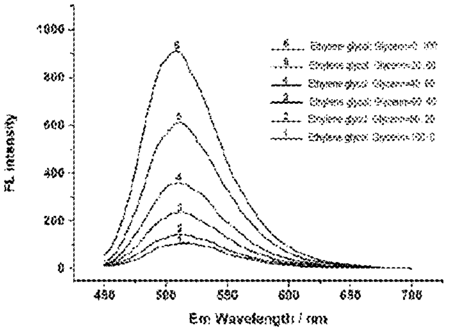
FIG. 1 is a diagram showing the fluorescence emission intensity at different viscosity conditions of the molecular rotor III-3 ($1\times10^{-5}$ M)

To a stirring solution of p-dimethylaminobenzaldehyde (0.35 g, 2.3 mmol) and 4-cyano-benzeneacetonitrile (0.4 g, 2.8 mmol) in 20 mL methanol, 2 drops of piperidine were added. After stirring at ambient temperature for 2 h, the mixture was cool to room temperature. A large amount of precipitate was appeared. Then the precipitate was obtained by filtration and washed with cold EtOH three times. The orange solid was obtained after dried under vacuum (0.60 g, yield 95%). $^1$H NMR (400 MHz, DMSO-$d_6$): δ=3.05 (s, 6H), 6.83 (d, J=9.2 Hz, 2H), 7.84-7.94 (m, 6H), 8.02 ppm (s, 1H). HRMS (ESI-TOF): Calcd. For $C_{18}H_{16}O_3$ $[M+H]^+$: 274.1344. Found: 274.1345.

Example 2

Compound III-2

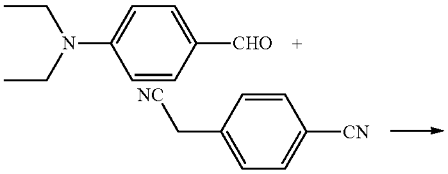

-continued

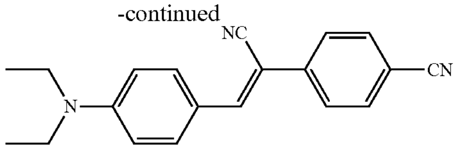

III-2

With reference to the synthetic method of compound III-1 (0.34, yield 89%). $^1$H NMR (400 MHz, DMSO-$d_6$): δ=1.23 (t, J=7.60 Hz, 6H), 3.05 (t, J=7.60 Hz, 4H), 6.84 (d, J=9.2 Hz, 2H), 7.84-7.95 (m, 6H), 8.09 ppm (s, 1H). HRMS (ESI-TOF): Calcd. For $C_{20}H_{20}O_3$ $[M+H]^+$: 302.1657. Found: 302.1658.

Example 3

Compound III-3

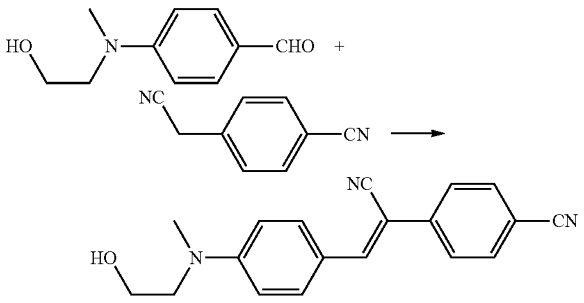

III-3

With reference to the synthetic method of compound III-1 (0.33 g, yield 95%). $^1$H NMR (400 MHz, DMSO-$d_6$): δ=7.96 (s, 1H), 7.85 (d, J=16.0 Hz, 6H), 6.81 (d, J=8.0 Hz, 2H), 4.77 (s, 1H), 3.55 (d, J=28.0 Hz, 4H), 3.04 (s, 1H). HRMS (ESI-TOF): Calcd. For $C_{19}H_{18}N_3O$ $[M+H]^+$: 304.1450. Found: 304.1451.

Example 4

Compound III-4

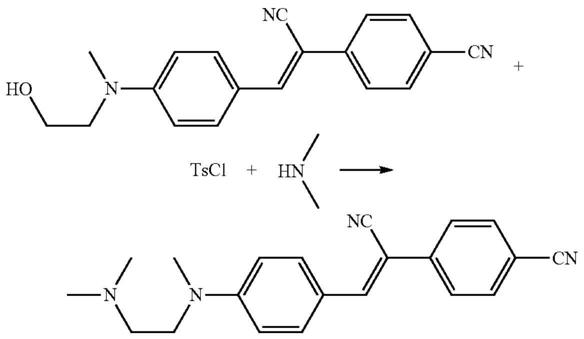

III-4

To stirring solution of compound III-3 (0.61 g, 2.0 mmol) and TEA (0.25 g, 2.2 mmol) in 40 mL dried DCM, 4-tosyl chloride (0.38 g, 2.0 mmol) in 10 mL DCM was added slowly under 0° C. The resulting mixture was stirred under Ar atom and was permitted to warm to room temperature. After complete the reaction, the mixture was quenched by 2 mL of water. The reaction mixture was extracted three times and the organic phase was dried with anhydrous $Na_2SO_4$ and evaporation under reduced pressure, the residue was used in the next step without purified.

To a stirring solution of the residue in 20 mL $CH_3CN$, 1 ml MeNH2 was added under Ar atmosphere. The mixture was heated to refluxed overnight. Upon completing the reaction, the reaction mixture was cooled to room temperature and the organic liquid was removed under reduce pressure. Then the residue was dissolved in 50 mL DCM and the organic phase was washed with water and brine (2×100 ml). Upon drying over anhydrous $Na_2SO_4$ and evaporation under reduced pressure, the residue was purified by column chromatography on silica gel to afford orange red solid. (0.54 g, 82%). $^1$H NMR (400 MHz, $CDCl_3$): δ=7.88 (d, J=9.0 Hz, 2H), 7.74-7.65 (m, 4H), 7.48 (s, 1H), 6.73 (d, J=9.1 Hz, 2H), 3.60-3.55 (m, 2H), 3.08 (s, 3H), 2.57-2.52 (m, 2H), 2.34 (s, 6H). HRMS (ESI-TOF): Calcd. For $C_{21}H_{23}N_4$ $[M+H]^+$: 331.1923. Found: 331.1925.

Example 5

Compound III-5

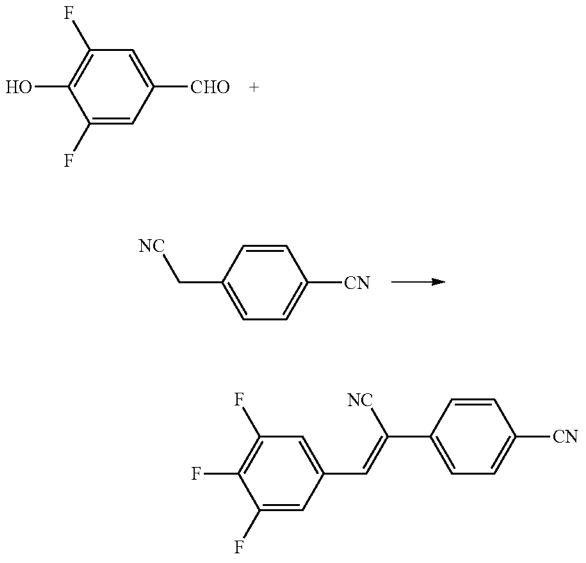

III-5

To a stirring solution of 3,5-difluoro-4-hydroxybenzaldehyde (0.32 g. 2.0 mmol) and 4-cyano-benzeneacetonitrile (0.35 g, 2.4 mmol) in 40 mL anhydrous EtOH, 2 drops of piperidine were added. After stirring at ambient temperature for 2 h, the mixture was cool to room temperature. A large amount of precipitate was appeared. Then the precipitate was obtained by filtration and washed with cold EtOH three times. The orange solid was obtained after dried under vacuum. $^1$H NMR (400 MHz, $CDCl_3$): δ=7.80 (d, J=9.0 Hz, 2H), 7.74-7.66 (m, 4H), 7.48 (s, 1H). HRMS (ESI-TOF): Calcd. For $C_{16}H_9F_2N_2O$ $[M+H]^+$: 283.0683. Found: 283.0684.

Example 6

Compound 5-(N-methyl-N-(2-hydroxyethyl)amino) pyrazine-2-carbaldehyde

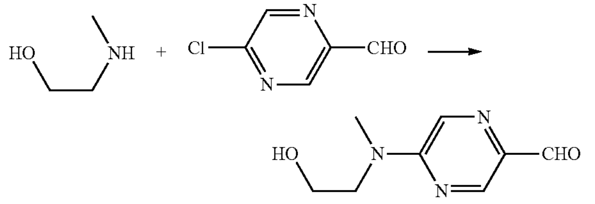

To a stirring solution of N-methyl-N-(2-hydroxyethyl) amino (2.6 g, 35 mmol) and 5-chloro-pyrazine-2-carbaldehyde (0.50 g, 3.5 mmol) in 20 mL dry $CH_3CN$, $K_2CO_3$ (0.71 g. 5.3 mmol) was added in one portion. The mixture was heated to reflux under Ar atmosphere. The mixture was heated to refluxed for 24 h. Upon completing the reaction, the reaction mixture was cooled to room temperature and the organic liquid was removed under reduce pressure. Then the residue was dissolved in 100 mL DCM and the organic phase was washed with water and brine (2×100 ml). Upon drying over anhydrous $Na_2SO_4$ and evaporation under reduced pressure, the residue was purified by column chromatography on silica gel to afford target compound. (0.48 g. 76%). $^1$H NMR (400 MHz, $CDCl_3$): δ 9.88 (s, 1H), 8.62 (d, J=1.2 Hz, 1H), 8.14 (d, J=1.1 Hz, 1H), 3.92 (m, 2H), 3.88-3.83 (m, 2H), 3.28 (s, 3H). HRMS (ESI-TOF): Calcd. For $C_8H_{12}N_3O_2$ $[M+H]^+$: 182.1. Found: 182.1.

Compound III-6

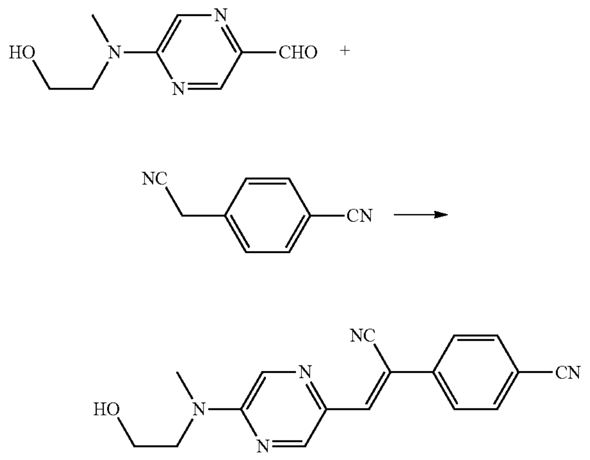

III-6

With reference to die synthetic method of compound III-1 (0.36 g. 96%). $^1$H NMR (400 MHz, $CDCl_3$): δ 8.39 (s, 1H), 8.30 (s, 1H), 7.80 (d, J=8.5 Hz, 2H), 7.72 (d, J=8.4 Hz, 2H), 7.51 (s, 1H), 3.93 (t, J=4.9 Hz, 2H), 3.88-3.83 (m, 2H), 3.29 (s, 3H). HRMS (ESI-TOF): Calcd. For $C_{17}H_{16}N_5O$ $[M+H]^+$: 306.1355. Found: 306.1357.

Example 7

Compound III-7

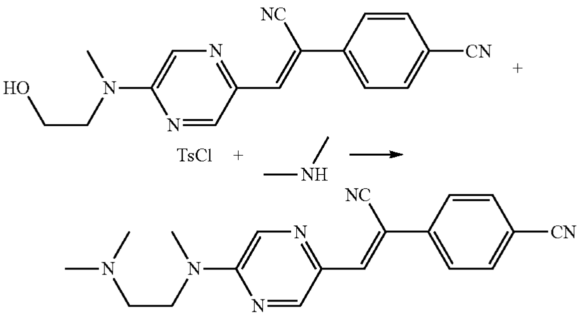

III-7

With reference to the synthetic method of compound III-4, (0.21 g, 67%). $^1$H NMR (400 MHz, DMSO-$d_6$): δ 8.37 (d, J=5.2 Hz, 2H), 8.06 (s, 1H), 8.00-7.85 (m, 4H), 3.77 (t, J=6.5 Hz, 2H), 3.20 (s, 3H), 2.56 (m, 2H), 2.23 (s, 6H). HRMS (ESI-TOF): Calcd. For $C_{19}H_{21}N_6$ $[M+H]^+$: 333.1828. Found: 333.1829.

Example 8

Compound 6-(N-methyl-N-(2-hydroxyethyl)amino) pyridine-2-carbaldehyde

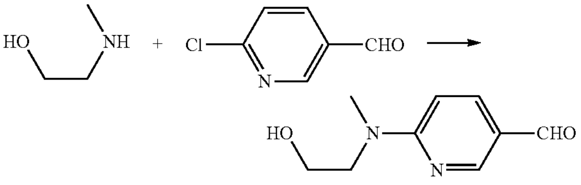

With reference to the synthetic method of Compound 5-(N-methyl-N-(2-hydroxyethyl)amino) pyrazine-2-carbaldehyde: (0.45 g, 68%). $^1$H NMR (400 MHz, $CDCl_3$): δ=9.69 (s, 1H), 8.43 (d, J=2.1 Hz, 1H), 7.86 (dd, J=9.0, 2.3 Hz, 1H), 6.56 (d, J=9.1 Hz, 1H), 3.86-3.79 (m, 4H), 3.15 (s, 3H). HRMS (ESI-TOF): Calcd. For $C_9H_{13}O_2N_2$ $[M+H]^+$: 181.1. Found: 181.1.

Compound III-8

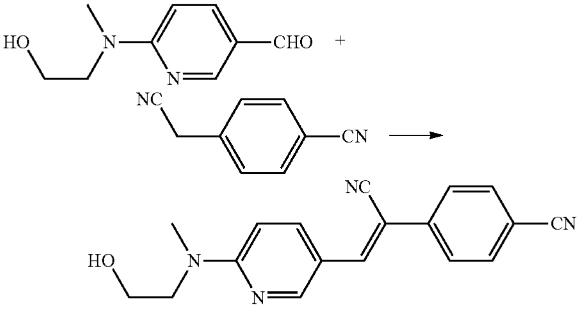

III-8

With reference to the synthetic method of compound III-1, (0.39 g, 89%). $^1$H NMR (400 MHz, DMSO-$d_6$): δ=8.54 (d, J=4.0 Hz, 1H), 8.30 (dd, J=9.3, 2.5 Hz, 1H), 8.03 (s, 1H), 7.92 (d, J=8.0 Hz, 2H), 7.85 (d, J=8.0 Hz, 2H), 6.84 (d, J=8.0 Hz, 1H), 4.77 (t, J=5.4 Hz, 1H), 3.67 (t, J=5.3 Hz, 2H), 3.60 (q, J=5.4 Hz, 2H), 3.15 (s, 3H). HRMS (ESI-TOF): Calcd. For $C_{18}H_{27}N_4O$ $[M+H]^+$: 305.1402. Found: 305.1401.

Example 9

Compound III-9

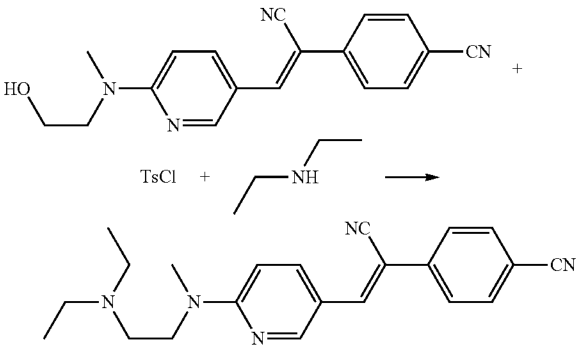

III-9

With reference to the synthetic method of compound III-4, (0.31 g, 92%). $^1$H NMR (400 MHz, DMSO-$d_6$): δ=8.55 (d, J=4.0 Hz, 1H), 8.31 (dd, J=9.3, 2.5 Hz, 1H), 8.05 (s, 1H), 7.93 (d, J=8.0 Hz, 2H), 7.84 (d, J=8.0 Hz, 2H), 6.85 (d, J=8.0 Hz, 1H), 4.78 (t, J=5.4 Hz, 1H), 3.67 (t, J=5.3 Hz, 2H), 3.60 (q, J=5.4 Hz, 2H), 3.17 (t, J=8.0 Hz, 4H), 1.17 (t, J=8.0 Hz, 6H). HRMS (ESI-TOF): Calcd. For $C_{22}H_{26}N_5$ $[M+H]^+$: 360.2188. Found: 360.2187.

Example 10

4-(N,N-dimethylamino)-pyrazine-6-carbaldehyde

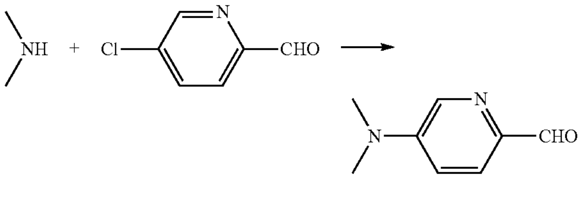

With reference to the synthetic method of compound III-4, (0.31 g, 49%). $^1$H NMR (400 MHz, DMSO-$d_6$): δ=9.86 (d, J=0.6 Hz, 1H), 8.17 (d, J=2.9 Hz, 1H), 7.83 (d, J=8.9 Hz, 1H), 6.94 (dd, J=8.8, 2.9 Hz, 1H), 3.10 (s, 6H). HRMS (ESI-TOF): Calcd. For $C_8H_{11}N_2O$ $[M+H]^+$: 151.1. Found: 151.1.

Compound III-10

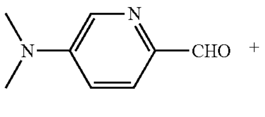

-continued

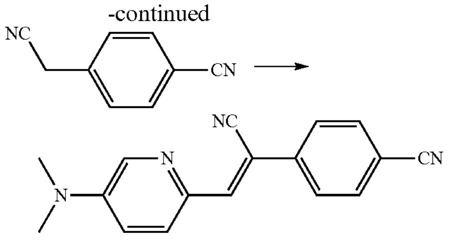

III-10

With reference to the synthetic method of compound III-1, (0.36 g. 96%). $^1$H NMR (400 MHz, DMSO-$d_6$): δ=9.86 (d, J=0.6 Hz, 1H), 8.26 (s, 1H), 8.17 (d, J=2.9 Hz, 1H), 7.83 (d, J=8.9 Hz, 1H), 7.46 (m, 4H), 6.94 (dd, J=8.8, 2.9 Hz, 1H), 3.10 (s, 6H). HRMS (ESI-TOF): Calcd. For $C_{17}H_{15}N_4$ $[M+H]^+$: 275.1297. Found: 275.1298.

Example 11

Compound 2-(N-methyl-N-(2-hydroxyethyl)amino) pyrimidine-5-carbaldehyde

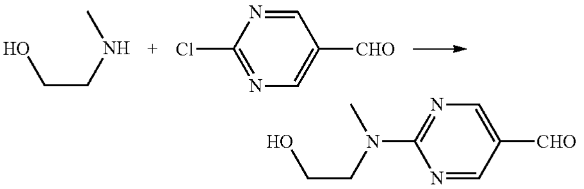

With reference to the synthetic method of compound III-4, (0.42 g, 72%). $^1$H NMR (400 MHz, DMSO-$d_6$): δ=9.89 (s, 1H), 8.73 (s, 2H), 3.64 (t, J=8.9 Hz, 2H), 3.45 (t, J=8.8 Hz, 2H), 3.10 (s, 3H). HRMS (ESI-TOF): Calcd. For $C_8H_{12}N_3O$ $[M+H]^+$: 182.1. Found: 182.1.

Compound III-11

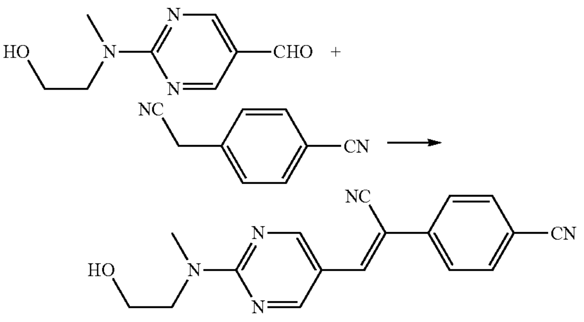

III-11

With reference to the synthetic method of compound III-1, (0.36 g, 96%). $^1$H NMR (400 MHz, DMSO-$d_6$): δ=8.26 (s, 1H), 8.73 (s, 2H), 7.64 (m, 4H), 3.64 (t, J=8.9 Hz, 2H), 3.44 (t, J=8.8 Hz, 2H), 3.11 (s, 3H). HRMS (ESI-TOF): Calcd. For $C_{17}H_{16}N_5O$ $[M+H]^+$: 306.1355. Found: 306.1356.

Example 12

Compound 5-(N-methyl-N-(2-hydroxyethyl)amino) pyrimidine-2-carbaldehyde

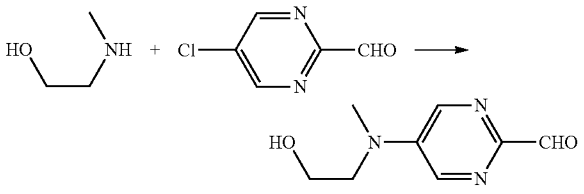

With reference to the synthetic method of compound III-4, (0.42 g. 72%). $^1$H NMR (400 MHz, DMSO-$d_6$): δ=9.98 (s, 1H), 8.21 (s, 2H), 3.64 (t, J=8.9 Hz, 2H), 3.44 (t, J=8.8 Hz, 2H), 3.12 (s, 3H). HRMS (ESI-TOF): Calcd. For $C_8H_{12}N_3O_2$ [M+H]$^+$: 182.1. Found: 182.1.

4-(1-cyano-2-(5-((2-hydroxyethyl)(methyl)amino) pyrimidin-2-yl)vinyl)benzonitrile

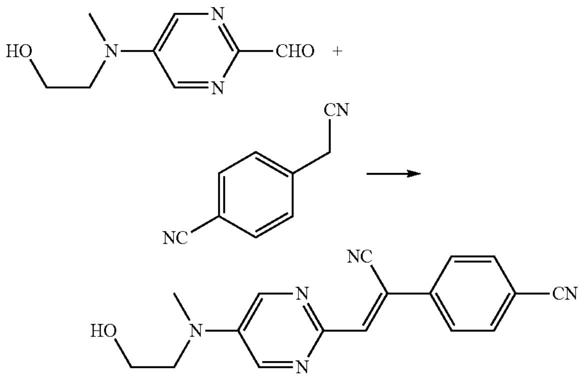

With reference to the synthetic method of compound III-1, (0.56 g, 89%). $^1$H NMR (400 MHz, DMSO-d): δ=8.21 (s. 2H), 7.99 (s, 1H), 7.64 (s, 4H), 3.64 (t, J=8.9 Hz, 2H), 3.44 (t, J=8.8 Hz, 2H), 3.12 (s, 3H). HRMS (ESI-TOF): Calcd. For $C_{17}H_{16}N_5O$ [M+H]$^+$: 306.1. Found: 306.1.

Compound III-12

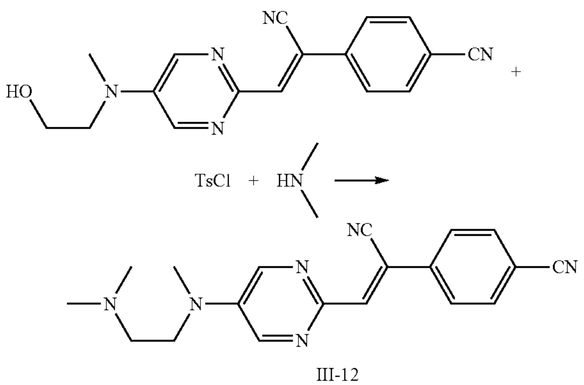

III-12

With reference to the synthetic method of compound III-4, (0.36 g, 96%). $^1$H NMR (400 MHz, DMSO-$d_6$): δ=8.21 (s, 2H), 7.99 (s, 1H), 7.64 (s, 4H), 3.77 (t, J=6.5 Hz, 2H), 3.20 (s, 3H), 2.56 (m, 2H), 2.23 (s, 6H). HRMS (ESI-TOF): Calcd. For $C_{19}H_{21}N_6$ [M+H]$^+$: 333.1828. Found: 333.1829.

Example 13

5-cyano-2-acetonitrile-pyridine

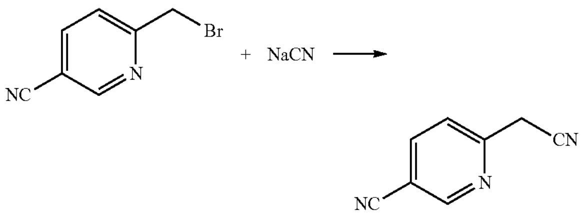

To a stirring solution of 2-(bromomethyl)-benzonitrile (0.50 g, 2.5 mmol) in 50 mL THF, 10 ml NaCN aqueous solution (2 M) was added. The mixture was reflexed for 12 h under Ar atmosphere. Upon cooling to room temperature, the reaction mixture was extracted with DCM (3×100 ml). The organic phase was washed with water and brine (2×100 ml). Upon drying over anhydrous $Na_2SO_4$ and evaporation under reduced pressure, the residue was purified by column chromatography on silica gel to afford target compound. (0.19 g, 56%). $^1$H NMR (400 MHz, DMSO-$d_6$): δ=8.78 (s, 1H), 7.95 (m, 1H), 7.56 (m, 1H), 4.01 (s, 2H). HRMS (ESI-TOF): Calcd. For $C_8H_6N_3$ [M+H]$^+$: 144.1. Found: 144.1.

Compound III-13

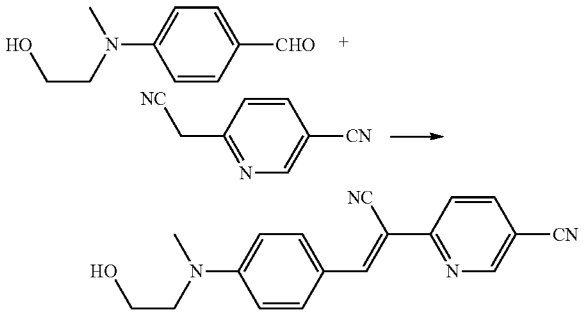

III-13

With reference to the synthetic method of compound III-1, (0.45 g, 95%). $^1$H NMR (400 MHz, DMSO-$d_6$): δ=8.78 (s, 1H), 8.21 (s, 1H), 7.94 (m, 1H), 7.86 (d, J=8.0 Hz, 2H), 7.57 (m, 1H), 6.80 (d, J=8.0 Hz, 2H), 3.64 (t, J=8.9 Hz, 2H), 3.44 (t, J=8.8 Hz, 2H), 3.12 (s, 3H). HRMS (ESI-TOF): Calcd. For $C_{18}H_{17}N_4O$ [M+H]$^+$: 305.1402. Found: 305.1403.

Example 14

5-cyano-2-acetonitrile-pyrazine

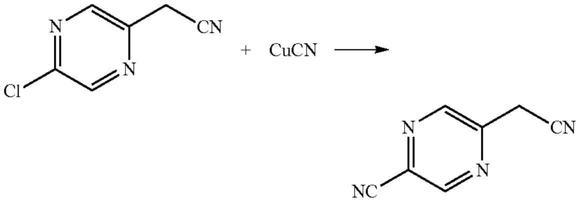

To a stirring solution of 2-(5-chloropyrazin-2-yl)acetonitrile (0.32 g, 2.0 mmol) in dry 30 mL DMSO, CuCN (0.93 g, 10.0 mmol) was added in one partition. The mixture was heated for 12 h under Ar atmosphere. Upon cooling to room temperature, the reaction mixture was poured into 100 mL water, then extracted with DCM (4×50 ml). The organic phase was washed with water and brine (2×100 ml). Upon drying over anhydrous $Na_2SO_4$ and evaporation under reduced pressure, the residue was purified by column chromatography on silica gel to afford target compound (0.20 g, 69%). $^1H$ NMR (400 MHz, DMSO-$d_6$): δ=8.60 (s, 1H), 8.48 (s, 1H), 3.92 (s, 2H). HRMS (ESI-TOF): Calcd. For $C_7H_5N_4$ $[M+H]^+$: 145.1. Found: 145.1.

Compound III-14

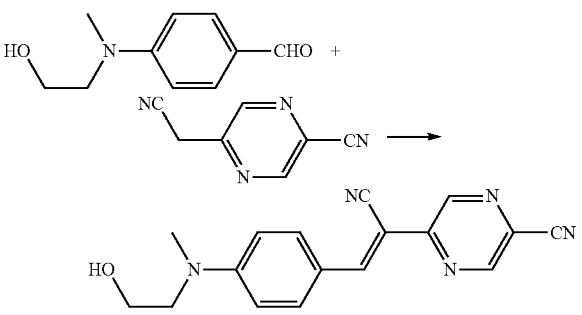

III-14

With reference to the synthetic method of compound III-1, (0.25 g, 91%). $^1H$ NMR (400 MHz, DMSO-$d_6$): δ=8.60 (s, 1H), 8.48 (s, 1H), 8.11 (s, 1H), 7.81 (d, J=8.2 Hz, 2H), 6.84 (d, J=8.2 Hz, 2H), 3.60 (t, J=9.2 Hz, 2H), 3.46 (t, J=9.2 Hz, 2H), 3.12 (s, 3H). HRMS (ESI-TOF): Calcd. For $C_{17}H_{16}N_5O$ $[M+H]^+$: 306.1355. Found: 306.1354.

Example 15

Compound III-15

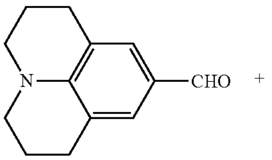

-continued

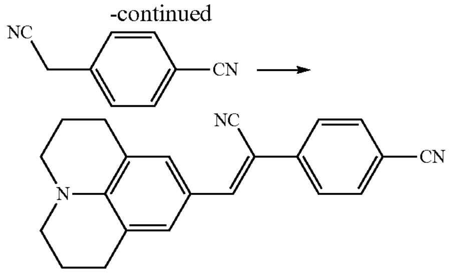

III-15

With reference to the synthetic method of compound III-1, (0.25 g, 91%). $^1H$ NMR (400 MHz, DMSO-$d_6$): δ=8.22 (s, 1H), 8.00 (d, J=9.1 Hz, 1H), 7.77-7.69 (m, 1H), 7.43-7.34 (m, 1H), 6.88 (d, J=9.1 Hz, 1H), 4.81 (t, J=5.2 Hz, 1H), 3.31-3.25 (m, 4H), 2.66-2.63 (m, 4H), 1.89-1.81 (m, 4H). HRMS (ESI-TOF): Calcd. For $C_{22}H_{20}N_3$ $[M+H]^+$: 326.1657. Found: 326.1658.

Example 16

Compound III-16

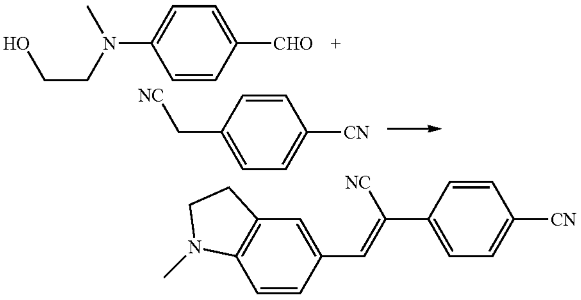

III-16

With reference to the synthetic method of compound III-1, (0.29 g, 94%). $^1H$ NMR (400 MHz, DMSO-$d_6$): δ=8.11 (2H, d, J=10.4 Hz), 7.99 (3H, dd, J=8.6, 3.0 Hz), 7.54 (1H, dd, J=8.0, 8.0 Hz), 7.44 (1H, dd, J=8.0, 8.0 Hz), 6.88 (2H, d, J=9.2 Hz), 4.82 (1H, bt, t, J=5.2 Hz), 3.01-3.08 (m, 2H), 3.53-3.60 (m, 2H), 2.89 (s, 3H). HRMS (ESI-TOF): Calcd. For $C_{19}H_{16}N_3$ $[M+H]^+$: 286.1344. Found: 286.1345.

Compound 17

6-(methylamino)benzo[b]thiophene-2-carbaldehyde

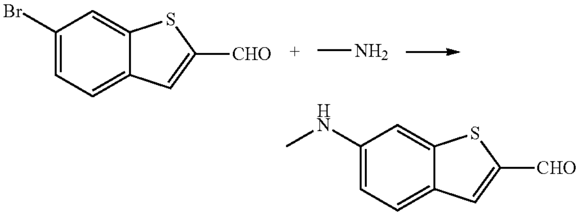

6-(methylamino)benzo[b]thiophene-2-carbaldehyde (0.42 g, 1.7 mmol), 40% aqueous N,N-Dimethylethylamine solution (1 g, 8.9 mmol), CuI (13.9 mg, 0.073 mmol), $K_3PO_4 \cdot H_2O$ (155.4 mg, 0.73 mmol), 1 mL 33% aqueous methylamine solution and stirring bar was sealed in a screwed tube and stirred at 60° C. for 12 h. upon cooling to room temperature, the mixture was poured into 50 mL water. The organic layer was separated and the aqueous layer was extracted with DCM (3×100 ml). Combined the organic phase and dried over anhydrous $Na_2SO_4$ and evaporation under reduced pressure, the residue was purified by column chromatography on silica gel to afford target compound (0.23 g, 68%). $^1$H NMR (400 MHz, DMSO-$d_6$): δ=9.92 (1H, s), 8.14 (1H, s), 7.82 (1H, d, J=9.1 Hz), 7.18 (1H, d, J=2.1 Hz), 7.01 (1H, dd, J=9.1, 2.3 Hz), 3.05 (3H, s). HRMS (ESI-TOF): Calcd. For $C_{10}H_{10}NOS$ [M+H]$^+$: 192.0. Found: 192.0.

Compound III-17

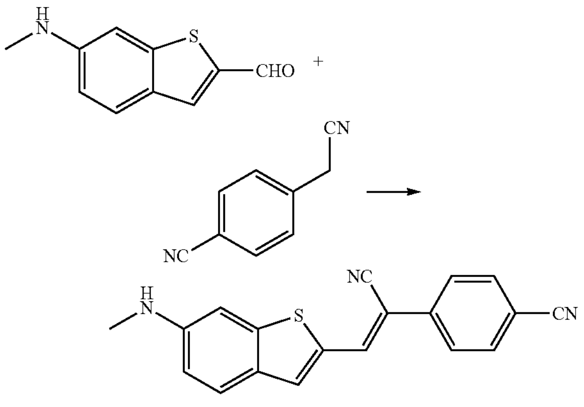

III-17

With reference to the synthetic method of compound III-1, (0.29 g, 94%). $^1$H NMR (400 MHz, DMSO-$d_6$): δ=8.45 (s, 1H), 7.92 (d, J=8.6 Hz, 2H), 7.85 (d, J=8.3 Hz, 3H), 7.73 (dd, J=8.6, 3.9 Hz, 1H), 7.21 (d, J=1.9 Hz, 1H), 7.21 (d, J=1.9 Hz, 1H), 6.96 (dd, J=9.1, 2.3 Hz, 1H), 3.05 (s, 3H). HRMS (ESI-TOF): Calcd. For $C_{19}H_{14}N_3S$ [M+H]$^+$: 360.1171. Found: 360.1173.

Example 18

6-((2-hydroxyethyl)(methyl)amino)benzo[b]thiophene-2-carbaldehyde

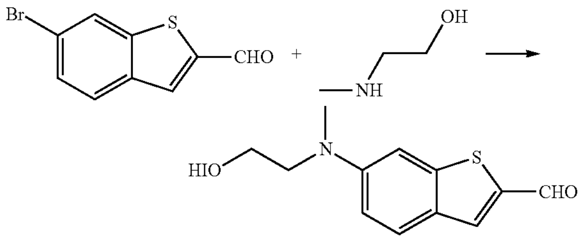

With reference to the synthetic method of compound 6-(methylamino)benzo[b]thiophene-2-carbaldehyde, (0.54 g, 79%). $^1$H NMR (400 MHz, DMSO-$d_6$): δ=9.91 (s, 1H), 8.14 (s, 1H), 7.81 (d, J=5.2 Hz, 1H), 7.17 (d, J=2.0 Hz, 1H), 7.01 (dd, J=2.0, 8.8 Hz, 1H), 4.76 (t, J=5.6 Hz, 1H), 3.58 (t, J=4.2 Hz, 2H), 3.52 (t, J=4.2 Hz, 2H), 3.04 (s, 3H). HRMS (ESI-TOF): m/z Calcd. For $C_{12}H_{14}NO_2S$, [M+H]$^+$: 235.1. Found 236.1.

Compound III-18

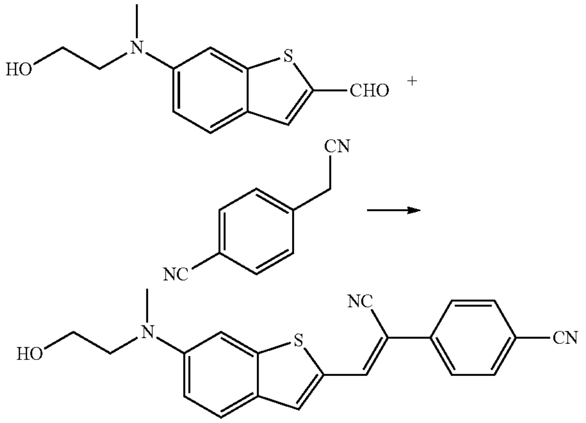

III-18

With reference to the synthetic method of compound III-1, (0.21 g, 95%). $^1$H NMR (400 MHz, DMSO-$d_6$): δ=8.45 (s, 1H), 7.92 (d, J=8.6 Hz, 2H), 7.85 (d, J=8.3 Hz, 3H), 7.73 (dd, J=8.6, 3.9 Hz, 1H), 7.21 (d, J=1.9 Hz, 1H), 7.21 (d, J=1.9 Hz, 1H), 1a 6.96 (dd, J=9.1, 2.3 Hz, 1H), 3.63-3.57 (m, 2H), 3.52 (t, J=5.7 Hz, 2H), 3.05 (s, 3H). HRMS (ESI-TOF): Calcd. For $C_{21}H_{19}N_3OS$ [M+H]$^+$: 360.1171. Found: 360.1173.

Example 19

5-(N,N-dimethylamino)-thieno[3,2-b]thiophene-2-carbaldehyde

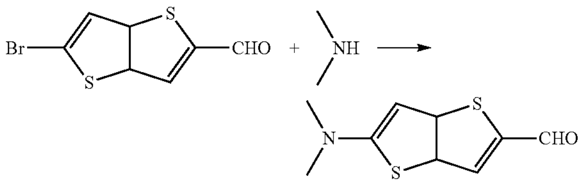

With reference to the synthetic method of compound 6-((2-hydroxyethyl)(methyl)amino)benzo[b]thiophene-2-carbaldehyde, (0.54 g, 79%). $^1$H NMR (400 MHz, DMSO-$d_6$): δ=9.66 (s, 1H), 8.05 (s, 1H), 6.30 (s, 1H), 4.88 (bt, 1H), 3.07 (s, 6H). HRMS (ESI-TOF): m/z Calcd. For $C_9H_{12}NOS_2$ [M+H]$^+$: 214.0; found 214.0.

Compound III-19

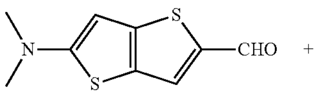

-continued

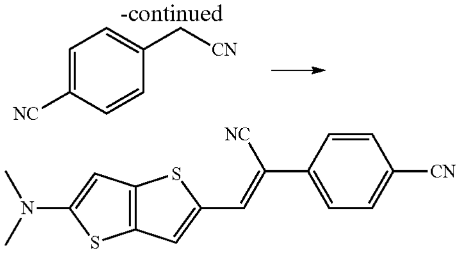

III-19

With reference to the synthetic method of compound III-1, (0.31 g, 90%). $^{1}$H NMR (400 MHz, DMSO-$d_6$): δ=8.34 (s, 1H), 7.86 (d, J=8.0 Hz, 2H), 7.81 (s, 1H), 7.77 (d, J=8.0 Hz, 2H), 6.32 (s, 1H), 4.88 (t, J=4.0 Hz, 1H), 3.08 (s, 6H). HRMS (ESI-TOF): Calcd. For $C_{18}H_{14}N_3S_2$ $[M+H]^+$: 336.0629. Found: 336.0630.

Example 20

5-(N,N-diethylamino)-thieno[3,2-b]thiophene-2-carbaldehyde

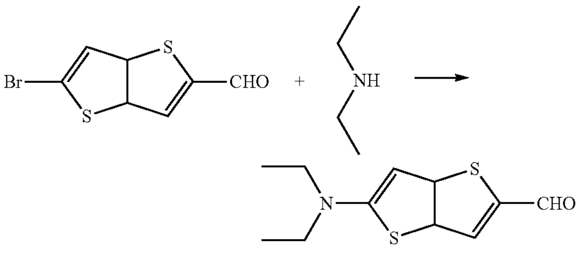

With reference to the synthetic method of compound 5-(N,N-dimethylamino)-thieno[3,2-b]thiophene-2-carbaldehyde, (0.44 g, 75%). $^{1}$H NMR (400 MHz, DMSO-$d_6$): δ=9.78 (s, 1H), 8.09 (s, 1H), 6.30 (s, 1H), 4.87 (bt, 1H), 3.27 (t, J=8.4 Hz, 4H), 1.26 (t, J=8.4 Hz, 4H). HRMS (ESI-TOF): m/z Calcd. For $C_9H_{12}NOS_2$ $[M+H]^+$: 214.0; found 214.0.

Compound III-20

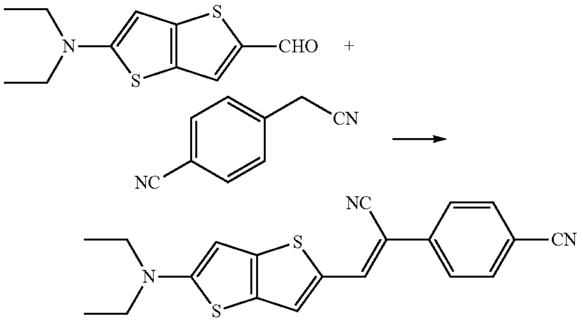

III-20

With reference to the synthetic method of compound III-1, (0.31 g, 90%). $^{1}$H NMR (400 MHz, DMSO-$d_6$): δ=8.34 (s, 1H), 7.86 (d, J=8.0 Hz, 2H), 7.81 (s, 1H), 7.77 (d, J=8.0 Hz, 2H), 6.32 (s, 1H), 4.88 (t, J=4.0 Hz, 1H), 3.27 (t, J=8.4 Hz, 4H), 1.26 (t, J=8.4 Hz, 4H). HRMS (ESI-TOF): Calcd. For $C_{20}H_{18}N_3S_2$ $[M+H]^+$: 364.0942. Found: 364.0943.

Example 21

5-((2-hydroxyethyl)(methyl)amino)-thieno[3,2-b]thiophene-2-carbaldehyde

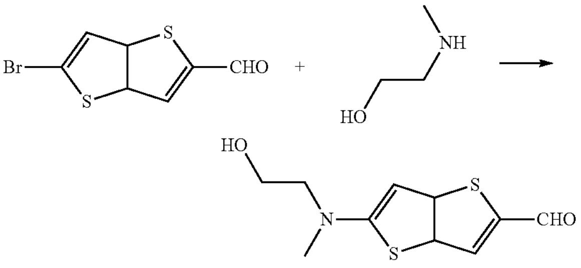

With reference to the synthetic method of compound 6-((2-hydroxyethyl)(methyl)amino)benzo[b]thiophene-2-carbaldehyde, (0.44 g, 75%). $^{1}$H NMR (400 MHz, DMSO-$d_6$): δ=9.66 (s, 1H), 8.05 (s, 1H), 6.30 (s, 1H), 4.88 (bt, 1H), 3.64 (t, J=5.6 Hz, 2H), 3.44 (t, J=5.6 Hz, 2H), 3.07 (s, 3H). HRMS (ESI-TOF): m/z Calcd. For $C_{10}H_{12}NO_2S_2$ $[M+H]^+$: 241.0; found 242.0.

Compound III-21

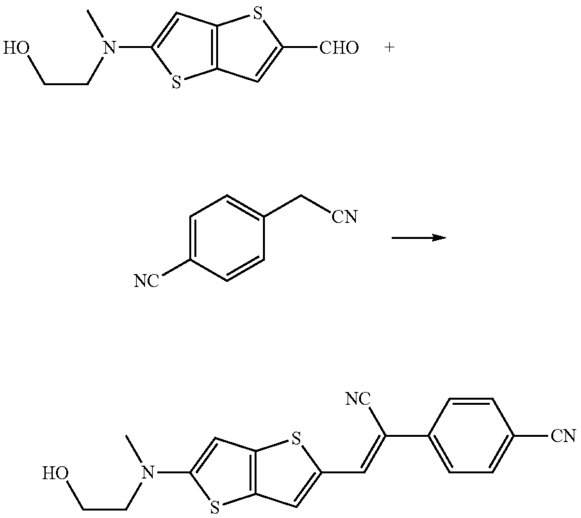

III-21

With reference to the synthetic method of compound III-1, (0.31 g, 90%). $^{1}$H NMR (400 MHz, DMSO-$d_6$): δ 8.34 (s, 1H), 7.86 (d, J=8.0 Hz, 2H), 7.81 (s, 1H), 7.77 (d, J=8.0 Hz, 2H), 6.32 (s, 1H), 4.88 (t, J=4.0 Hz, 1H), 3.65 (q, J=5.5 Hz, 2H), 3.44 (t, J=5.5 Hz, 2H), 3.34 (s, 1H), 3.08 (s, 3H). HRMS (ESI-TOF): Calcd. For $C_{19}H_{16}N_3OS_2$ $[M+H]^+$: 366.0735. Found: 366.0736.

Example 22

Compound III-22

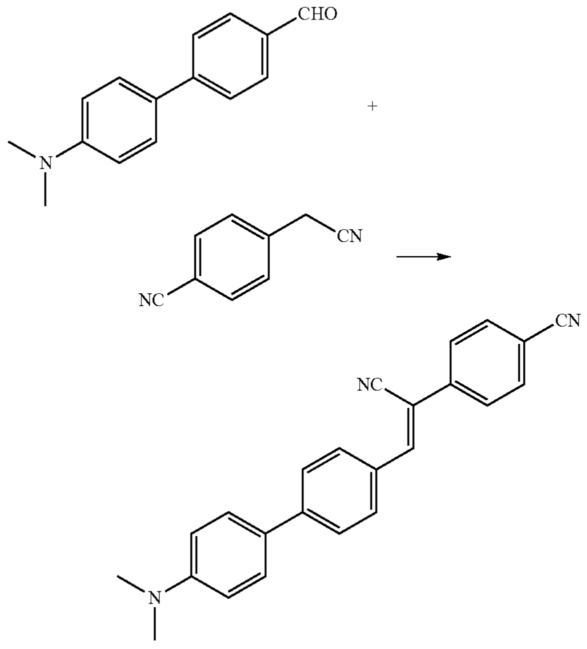

III-22

With reference to the synthetic method of compound III-1, (0.31 g, 90%). $^1$H NMR (400 MHz, DMSO-$d_6$): δ=3.04 (s, 6H), 6.82 (d, J=9.2 Hz, 2H), 7.59 (d, J=9.1 Hz, 2H), 7.84-7.94 (m, 6H), 8.02 ppm (s, 1H). HRMS (ESI-TOF): Calcd. For $C_{24}H_{19}O_3$ $[M+H]^+$: 350.1657. Found: 350.1656.

Example 23

Compound III-23

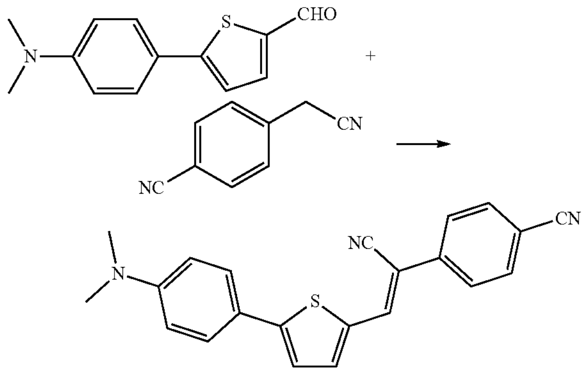

III-23

With reference to the synthetic method of compound III-1: $^1$H NMR (400 MHz, DMSO-$d_6$): δ=3.02 (s, 6H), 6.72 (d, J=8.0 Hz, 2H), 7.24 (d, J=4.0 Hz, 1H), 7.49 (d, J=8.8 Hz, 2H), 7.55 (d, J=8.0 Hz, 1H), 7.69 (d, J=8.8 Hz, 2H), 8.02 ppm (s, 1H). HRMS (ESI-TOF): Calcd. For $C_{22}H_{18}N_3S$ $[M+H]^+$: 356.1221. Found: 356.1220.

Example 24

Compound III-24

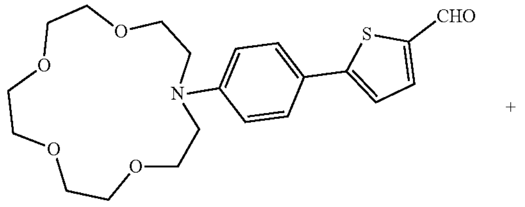

Compound 1

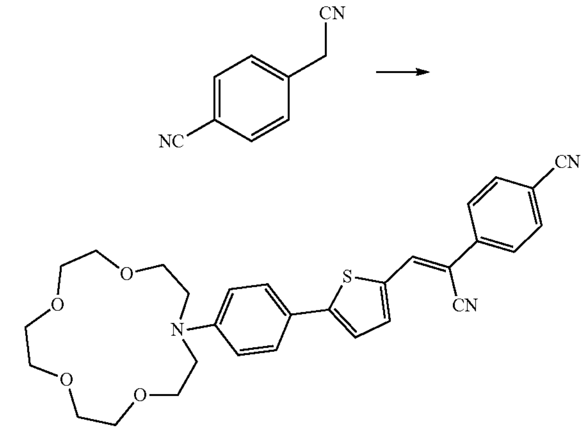

III-24

With reference to the synthetic method of compound III-1, and compound 1 (With reference to the synthetic method of Chem. Commun. 2011, 47, 985-987): $^1$H NMR (400 MHz, DMSO-$d_6$): δ=3.63 (m, 16H), 3.77 (m, 4H), 6.76 (d, J=8.8 Hz, 2H), 7.38 (d, J=4.0 Hz, 2H), 7.49 (d, J=8.8 Hz, 2H), 7.59 (d, J=8.8 Hz, 2H), 7.72 (m, 4H), 8.28 (s, 1H). HRMS (ESI-TOF): Calcd. For $C_{30}H_{32}N_4S$ $[M+H]^+$: 530.2114. Found: 530.2115.

Example 25

Compound III-25

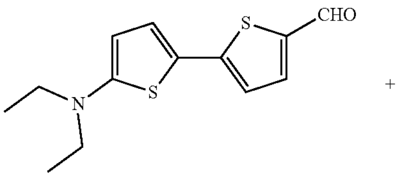

Compound 2

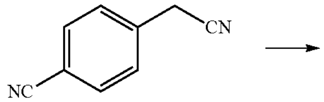

-continued

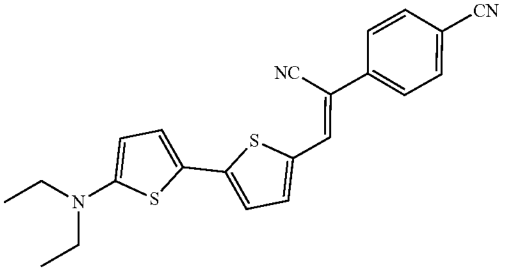

III-25

With reference to the synthetic method of compound III-1, and compound 2 (With reference to the synthetic method of J. Org. Chem. 2008, 73, 6587-6594): $^1$H NMR (400 MHz, DMSO-$d_6$): δ=1.23 (t, J=7.2 Hz, 6H), 3.35 (m, J=7.2 Hz, 4H), 5.78 (d, J=4.0 Hz, 1H), 6.92 (d, J=4.0 Hz, 1H), 7.12 (d, 1=4.0 Hz, 1H), 7.49 (d, J=8.8 Hz, 2H), 7.56 (d, J=4.0 Hz, 1H), 7.69 (d, J=8.8 Hz, 2H), 8.28 (s, 1H). HRMS (ESI-TOF): Calcd. For $C_{30}H_{32}O_3N_4S$ $[M+H]^+$: 390.1099. Found: 390.1097.

Example 26

Compound III-26

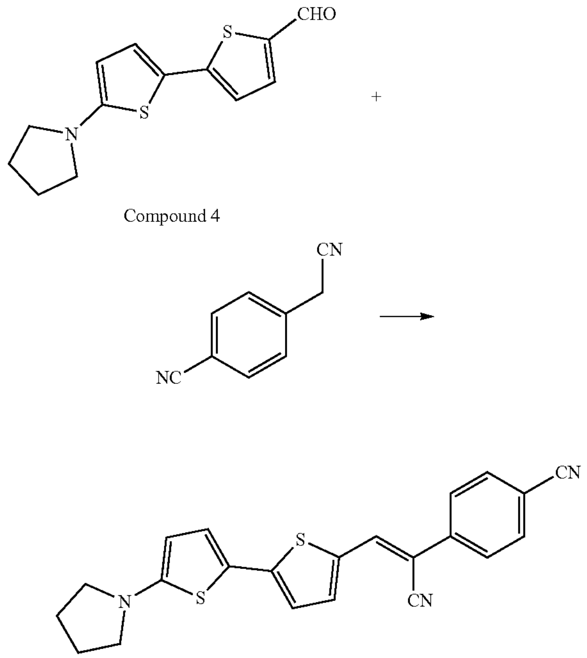

Compound 4

III-27

With reference to the synthetic method of compound III-1, $^1$H NMR (400 MHz, DMSO-$d_6$): δ=3.30 (s, 6H), 5.71 (d, J=4.0 Hz, 1H), 6.93 (d, J=4.0 Hz, 1H), 7.15 (d, J=4.0 Hz, 1H), 7.47 (d, J=8.8 Hz, 2H), 7.56 (d, J=4.0 Hz, 1H), 7.64 (d, J=8.8 Hz, 2H), 8.28 (s, 1H). HRMS (ESI-TOF): Calcd. For $C_{20}H_{17}O_2N_2S_2$ $[M+H]^+$: 381.0731. Found: 381.0730.

Example 27

Compound III-27

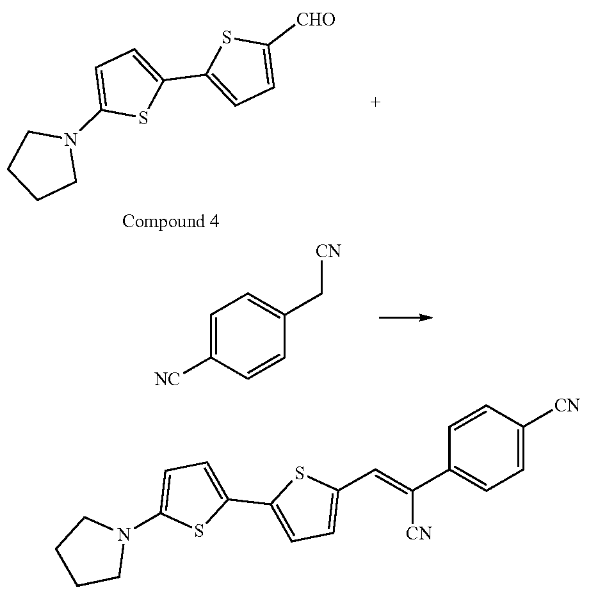

Compound 4

III-27

With reference to the synthetic method of compound III-1, and compound 4 (With reference to the synthetic method of Heterocycles, 1997, 46, 489-501) $^1$H NMR (400 MHz, $CDCl_3$): δ 2.07 (m, 4H), 3.33 (t, J=6.6 Hz, 4H), 4.2 (s, 3H), 5.70 (d, J=4.4 Hz, 1H), 6.92 (d, J=4.0 Hz, 1H), 7.15 (d, J=4.0 Hz, 1H), 7.43 (d, J=8.2 Hz, 2H), 7.51 (d, J=8.2 Hz, 2H), 7.57 (d, J=4.0 Hz, 1H), 8.10 (s, 1H). HRMS (ESI-TOF): Calcd. For $C_{23}H_{21}O_2N_2S_2[M+H]^+$: 421.1044. Found: 521.1042.

Example 28

Compound III-28

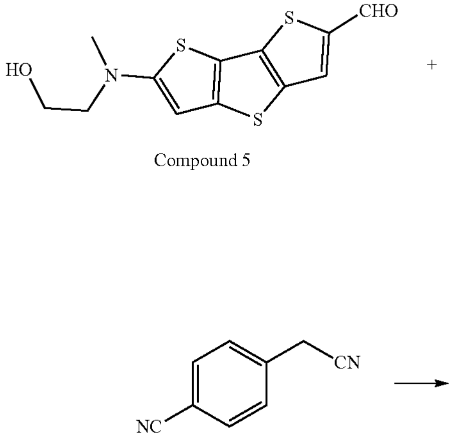

Compound 5

-continued

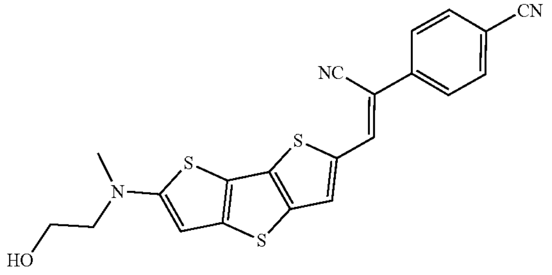

III-28

With reference to the synthetic method of compound III-1, and compound 5 (With reference to the synthetic method of WO2018014821). $^1$H-NMR (400 MHz, DMSO-$d_6$): δ=7.84 (s, 1H), 7.59 (d, J=8.8 Hz, 2H), 7.49 (d, J=8.8 Hz, 2H), 7.24 (s, 1H), 3.78 (t, 2H, J=4.80 Hz), 3.44 (t, 2H, J=4.80 Hz), 3.02 (s, 3H). HRMS (ESI-TOF): Calcd. For $C_{21}H_{16}ON_3S_3$. $[M+H]^+$: 422.0455. Found: 422.0456.

Example 29

Compound III-29

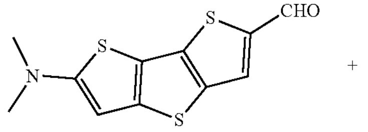

Compound 6

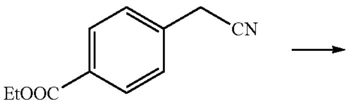

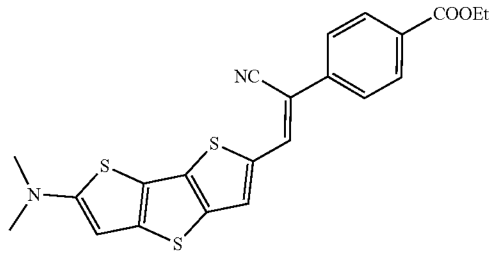

III-29

With reference to the synthetic method of compound III-1, and compound 6 (With reference to the synthetic method of WO2018014821). $^1$H-NMR (400 MHz, DMSO-$d_6$): δ=7.84 (s, 1H) 7.59 (d, J=8.8 Hz, 2H), 7.49 (d, J=8.8 Hz, 2H), 7.24 (s, 1H), 3.56 (q, J=4.0 Hz, 2H), 3.01 (s, 6H), 1.21 (t, J=4.0 Hz, 3H). HRMS (ESI-TOF): Calcd. For $C_{22}H_{19}O_2N_2S_3$. $[M+H]^+$: 439.0609. Found: 439.0610.

Example 30

Compound III-30

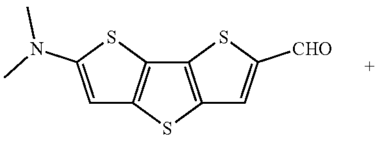

Compound 6

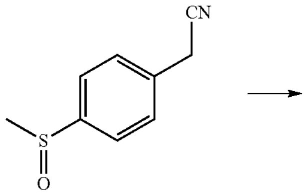

Compound 7

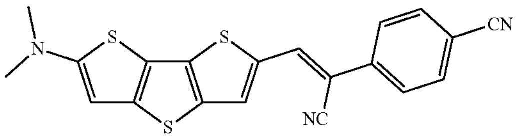

III-30

With reference to the synthetic method of compound III-1, and compound 7 (With reference to the synthetic method of WO 2014048547). $^1$H-NMR (400 MHz, DMSO-$d_6$): δ=7.84 (s, 1H), 7.59 (d, J=8.8 Hz, 2H), 7.49 (d, J=8.8 Hz, 2H), 7.24 (s, 1H), 3.10 (s, 3H), 3.01 (s, 6H). HRMS (ESI-TOF): Calcd. For $C_{21}H_{17}O_1N_2S_4$. $[M+H]^+$: 429.0024. Found: 429.0026.

Example 31

Compound III-31

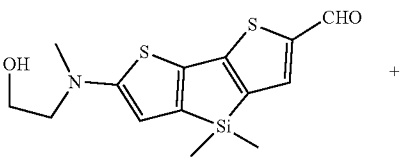

Compound 10

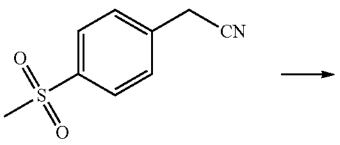

-continued

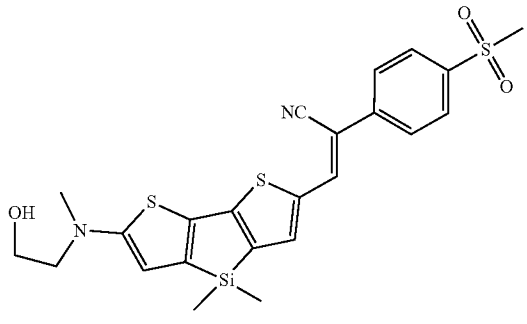

III-31

With reference to the synthetic method of compound III-1, and compound 9 (With reference to the synthetic method of J. Chem. Pharm. Res., 2012, 4, 1661-1669). $^1$H-NMR (400 MHz, DMSO-$d_6$): δ=7.84 (s, 1H), 7.59 (d, J=8.8 Hz, 2H), 7.49 (d, J=8.8 Hz, 2H), 7.24 (s, 1H), 3.14 (s, 3H), 3.01 (s, 6H). HRMS (ESI-TOF): Calcd. For $C_{22}H_{23}O_2N_2S_3Si$. $[M+H]^+$: 471.0691. Found: 471.0690.

Example 32

Compound III-32

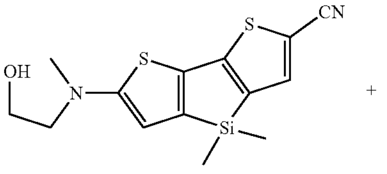

Compound 10

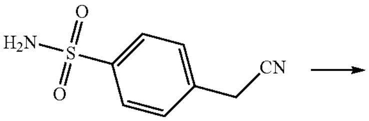

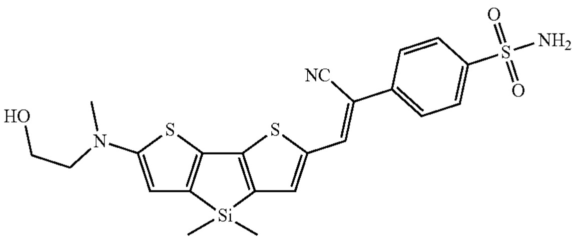

III-32

With reference to the synthetic method of compound III-1. $^1$H-NMR (400 MHz, DMSO-$d_6$): δ=7.84 (s, 1H), 7.59 (d, J=8.8 Hz, 2H), 7.49 (d, J=8.8 Hz, 2H), 7.24 (s, 1H), 3.77 (t, 2H, J=4.80 Hz), 3.41 (t, 2H, J=4.80 Hz), 3.00 (s, 3H). HRMS (ESI-TOF): Calcd. For $C_{22}H_{24}O_3N_3S_3Si$. $[M+H]^+$: 502.0749. Found: 502.0752.

Example 33

Compound III-33

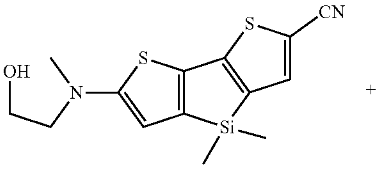

Compound 10

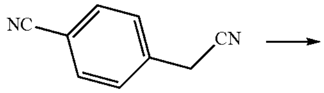

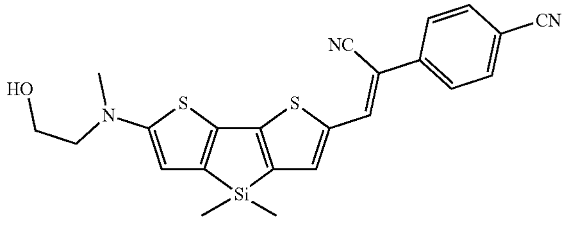

III-33

With reference to the synthetic method of compound III-1. $^1$H-NMR (400 MHz, $CDCl_3$): δ=7.89 (s, 1H), 7.59 (d, J=8.8 Hz, 2H), 7.49 (d, J=8.8 Hz, 2H), 7.18 (s, 1H), 6.96 (d, 2H, J=5.6 Hz), 3.85 (t, 2H, J=4.80 Hz), 3.46 (t, 2H, J=4.80 Hz), 3.06 (s, 3H), 0.46 (s, 6H). Calcd. For $C_{23}H_{22}ON_3S_2Si$. $[M+H]^+$: 448.0974. Found: 448.0972.

Example 34

Compound III-34

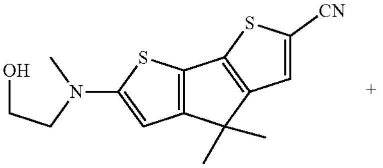

Compound 11

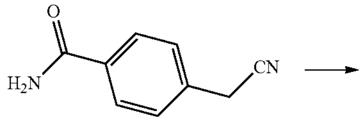

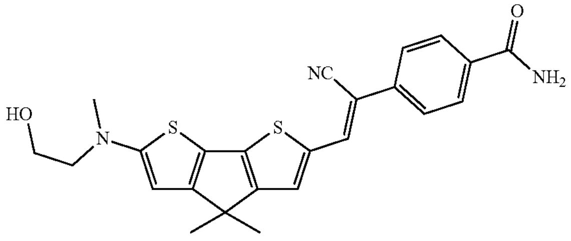

III-34

With reference to the synthetic method of compound III-1. $^1$H-NMR (400 MHz, $CDCl_3$): δ=7.83 (s, 1H), 7.59 (d, 1=8.8 Hz, 2H), 7.49 (d, J=8.8 Hz, 2H), 7.11 (s, 1H), 3.85 (t, 2H, J=4.80 Hz), 3.46 (t, 2H, J=4.80 Hz), 3.06 (s, 3H), 1.46 (s, 6H). HRMS (ESI-TOF): Calcd. For $C_{24}H_{24}O_2N_3S_2$ $[M+H]^+$:450.1310. Found: 450.1311.

Example 35

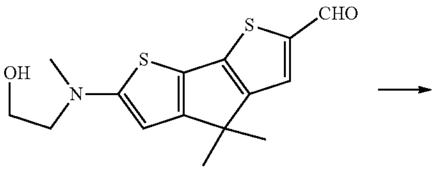

Compound 11

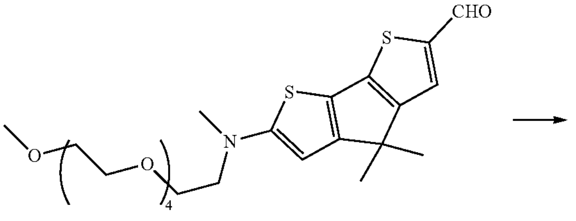

Compound 12

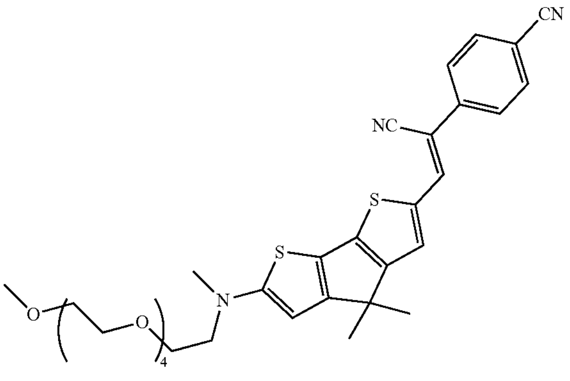

III-35

Compound 12

With reference to the synthetic method of (K. T. Arun et. al. J. Phys. Chem. A. 2005, 109, 5571-5578.) $^1$H-NMR (400 MHz, CDCl3): δ=10.01 (s, 1H), 7.89 (s, 1H), 7.18 (s, 1H), 6.96 (d, 2H, J=5.6 Hz), 3.52-3.65 (m, 20H), 3.37 (s, 3H), 2.97 (s, 3H). HRMS (ESI-TOF): Calcd. For $C_{24}H_{22}ON_3S_2Si$. $[M+H]^+$:432.1204. Found: 432.1203. Calcd. For $C_{24}H_{36}O_6N_1S_2$. $[M+H]^+$: 497.3. Found: 497.3.

Compound III-35

With reference to the synthetic method of compound III-1. $^1$H-NMR (400 MHz, $CDCl_3$): δ=7.89 (s, 1H), 7.59 (d, J=8.8 Hz, 2H), 7.49 (d, J=8.8 Hz, 2H), 7.18 (s, 1H), 6.96 (d, 2H, 1=5.6 Hz), 3.52-3.65 (m, 20H), 3.37 (s, 3H), 2.97 (s, 3H). HRMS (ESI-TOF): Calcd. For $C_{33}H_{39}O_5N_3S_2$. $[M+H]^+$: 622.2409. Found: 622.2409.

Control Example 1

Compound III-36

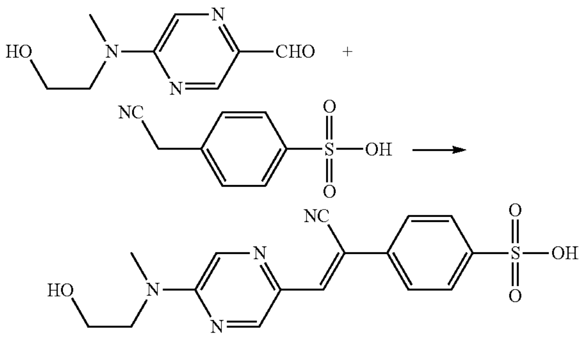

III-36

With reference to the synthetic method of compound III-1, (0.25 g, 91%). $^1$H NMR (400 MHz, DMSO-$d_6$): δ=8.21 (s, 2H), 7.99 (s, 1H), 7.64 (s, 4H), 3.64 (t, J=8.9 Hz, 2H), 3.44 (t, J=8.8 Hz, 2H), 3.12 (s, 3H). HRMS (ESI-TOF): Calcd. For $C_{16}H_{17}N_4O_4S$ $[M+H]^+$: 361.0971. Found: 361.0970.

Control Example 2

Compound III-37

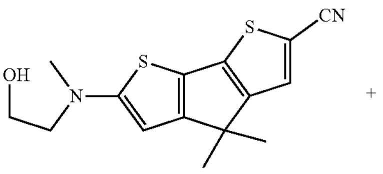

Compound 11

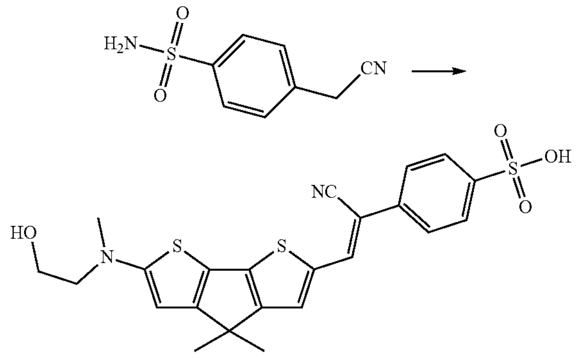

III-37

With reference to the synthetic method of compound III-1, (0.39 g. 91%). $^1$H NMR (400 MHz, DMSO-$d_6$): δ=7.83 (s, 1H), 7.59 (d, J=8.8 Hz, 2H), 7.49 (d, J=8.8 Hz, 2H), 7.11 (s, 1H), 3.85 (t, 2H, J=4.80 Hz), 3.46 (t, 2H, J=4.80 Hz), 3.05 (s, 3H), 1.46 (s, 6H). HRMS (ESI-TOF): Calcd. For $C_{23}H_{23}N_2O_4S_3[M+H]^+$: 487.0820. Found: 487.0821.

Control Example 3

Compound III-38

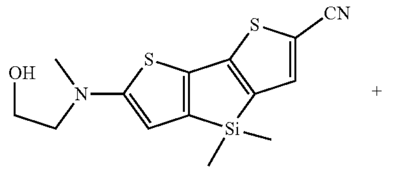

Compound 11

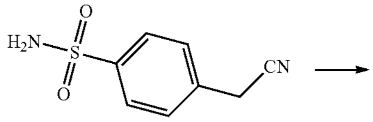

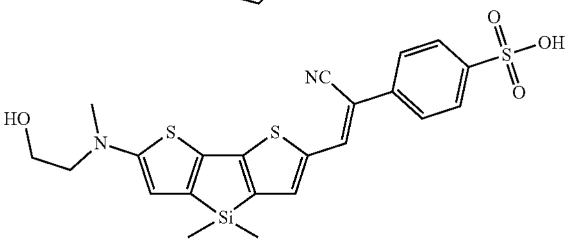

III-38

With reference to the synthetic method of compound III-1, and compound 11 (With reference to the synthetic method of CN 106349105). $^1$H-NMR (400 MHz, DMSO-$d_6$): δ=7.84 (s, 1H), 7.59 (d, J=8.8 Hz, 2H), 7.49 (d, J=8.8 Hz, 2H), 7.24 (s, 1H), 3.78 (t, 2H, J=4.80 Hz), 3.44 (t, 2H, J=4.80 Hz), 3.01 (s, 3H). HRMS (ESI-TOF): Calcd. For $C_{22}H_{23}O_4N_2S_3Si$. $[M+H]^+$: 503.0589. Found: 203.0588.

Control Example 4

Compound III-39

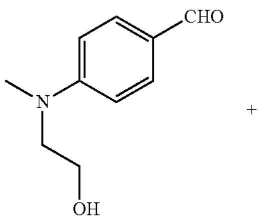

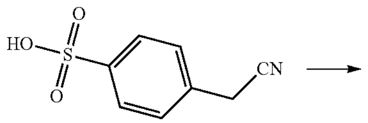

-continued

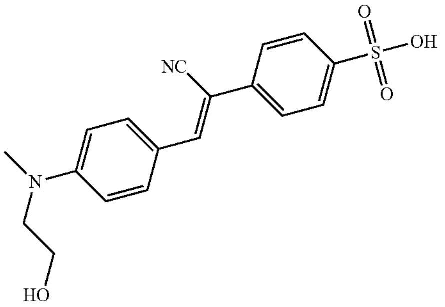

III-39

With reference to the synthetic method of compound III-1. $^1$H-NMR (400 MHz, DMSO-$d_6$): δ=7.84 (s, 1H), 7.59 (d, J=8.8 Hz, 2H), 7.49 (d, J=8.8 Hz, 2H), 3.78 (t, 2H, J=4.80 Hz), 3.44 (t, 2H, J=4.80 Hz), 3.01 (s, 3H). HRMS (ESI-TOF): Calcd. For $C_{18}H_{19}O_4N_2S$. $[M+H]^+$: 359.1066. Found: 359.1065.

Control Example 5

Compound III-40

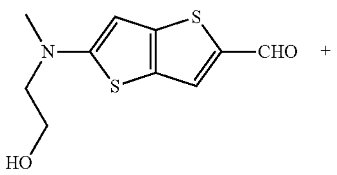

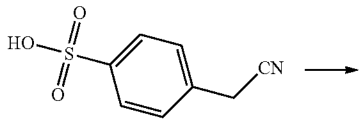

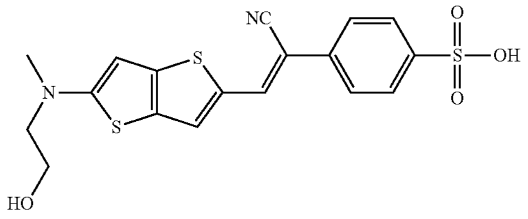

III-40

With reference to the synthetic method of compound III-1. $^1$H-NMR (400 MHz, DMSO-$d_6$): δ=8.34 (s, 1H), 7.59 (d, J=8.0 Hz, 2H), 7.81 (s, 1H), 7.49 (d, J=8.0 Hz, 2H), 6.32 (s, 1H), 4.88 (t, J=4.0 Hz, 1H), 3.65 (q, J=5.5 Hz, 2H), 3.44 (t, J=5.5 Hz, 2H), 3.34 (s, 1H), 3.08 (s, 3H). HRMS (ESI-TOF): Calcd. For $C_{18}H_{17}O_4N_2S_3$. $[M+H]^+$: 421.0350. Found: 421.0351.

Control Example 6

Compound III-41

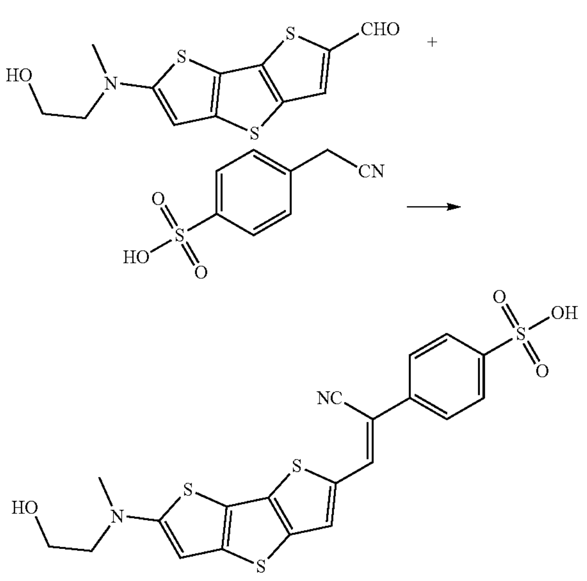

III-41

With reference to the synthetic method of compound III-1. $^{1}$H-NMR (400 MHz, DMSO-$d_6$): δ=7.85 (s, 1H), 7.59 (d, J=8.8 Hz, 2H), 7.47 (d, J=8.8 Hz, 2H), 7.24 (s, 1H), 3.79 (t, 2H, J=4.80 Hz), 3.43 (t, 2H, J=4.80 Hz), 3.01 (s, 3H). HRMS (ESI-TOF): Calcd. For $C_{20}H_{17}O_4N_2S_4$. $[M+H]^+$: 477.0071. Found: 477.0070.

Control Example 7

Compound III-42

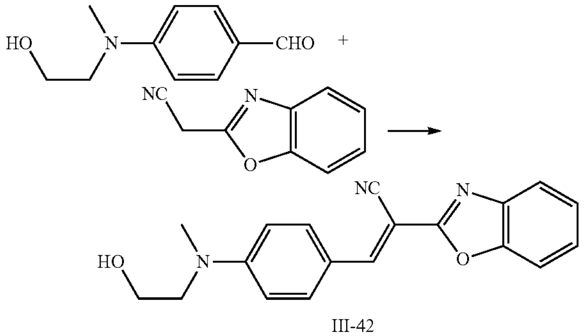

III-42

With reference to the synthetic method of compound III-1, (0.25 g, 91%). $^{1}$H NMR (400 MHz, DMSO-$d_6$): δ=8.22 (s, 1H), 8.00 (d, J=9.1 Hz, 1H), 7.77-7.69 (m, 1H), 7.43-7.34 (m, 1H), 6.88 (d, J=9.1 Hz, 1H), 4.81 (t, J=5.2 Hz, 1H), 3.64-3.52 (m, 3H), 3.09 (s, 1H). LR-HRMS (ESI-TOF): Calcd. For $C_{19}H_{18}N_3O_2[M+H]^+$: 320.1399. Found: 320.1397.

Control Example 8

Compound III-43

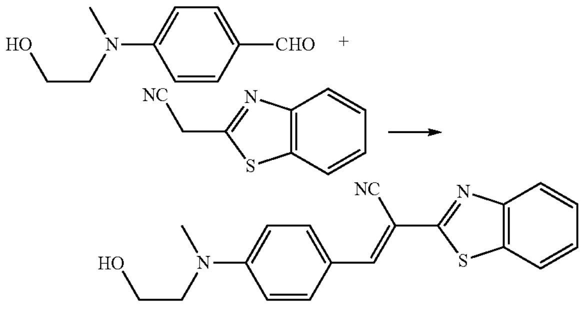

III-43

With reference to the synthetic method of compound III-1, (0.29 g, 94%). $^{1}$H NMR (400 MHz, DMSO-$d_6$): δ=8.11 (2H, d, J=10.4 Hz), 7.99 (3H, dd, J=8.6, 3.0 Hz), 7.54 (1H, dd, J=8.0, 8.0 Hz), 7.44 (1H, dd, J=8.0, 8.0 Hz), 6.88 (2H, d, J=9.2 Hz), 4.82 (1H, bt, t, J=5.2 Hz), 3.60 (2H, t, J=5.2 Hz), 3.56 (2H, t, J=5.2 Hz), 3.09 (3H, s). LR-HRMS (ESI-TOF): Calcd. For $C_{19}H_{18}N_3OS$ $[M+H]^+$: 336.1171. Found: 336.1170.

Test Example 1

The fluorescent dyes (molecular rotors) prepared in Examples 1-35 were dissolved in DMSO with a concentration of $1\times10^{-2}$ M each, and each master batch was added to glycerol and methanol respectively, mixed well, and a solution with a final concentration of 1x10-5 M each was prepared. According to the different fluorescent dyes, the fluorescence emission pattern of each fluorescent dye was detected under the same conditions using the maximum excitation wavelength of each fluorescent dye in turn, and the results are shown in Table 1, indicating that the fluorescent dyes of the present invention are sensitive to changes in viscosity.

TABLE 1

| Compound | Emission (nm) | Glycerol/methanol fluorescence intensity ratio |
|---|---|---|
| III-1 | 530 | 990 |
| III-2 | 530 | 870 |
| III-3 | 530 | 1025 |
| III-4 | 521 | 892 |
| III-5 | 525 | 1028 |
| III-6 | 490 | 1148 |
| III-7 | 485 | 977 |
| III-8 | 495 | 1168 |
| III-9 | 490 | 920 |
| III-10 | 520 | 1620 |
| III-11 | 470 | 869 |
| III-12 | 542 | 855 |
| III-13 | 545 | 752 |
| III-14 | 550 | 785 |
| III-15 | 561 | 1011 |
| III-16 | 555 | 491 |
| III-17 | 587 | 828 |
| III-18 | 595 | 978 |
| III-19 | 620 | 991 |
| III-20 | 620 | 836 |
| III-21 | 620 | 544 |

TABLE 1-continued

| Compound | Emission (nm) | Glycerol/methanol fluorescence intensity ratio |
|---|---|---|
| III-22 | 650 | 989 |
| III-23 | 661 | 687 |
| III-24 | 662 | 596 |
| III-25 | 678 | 783 |
| III-26 | 676 | 368 |
| III-27 | 678 | 486 |
| III-28 | 662 | 559 |
| III-29 | 665 | 684 |
| III-30 | 660 | 756 |
| III-31 | 687 | 624 |
| III-32 | 690 | 817 |
| III-33 | 705 | 691 |
| III-34 | 689 | 489 |
| III-35 | 690 | 710 |

Test Example 2

Figure 2:
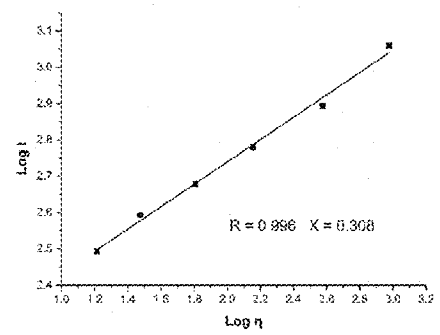
FIG. 2 is a diagram showing the linear relationship between viscosity conditions and fluorescence intensity of the molecular rotor III-3 ($1\times10^{-5}$ M)
Figure 3:
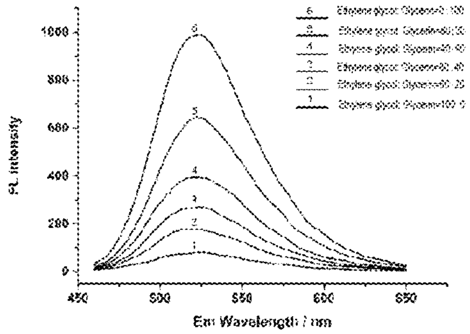
FIG. 3 is a diagram showing the fluorescence emission intensity at different viscosity conditions of the molecular rotor III-4 ($1\times10^{-5}$ M)
Figure 4:
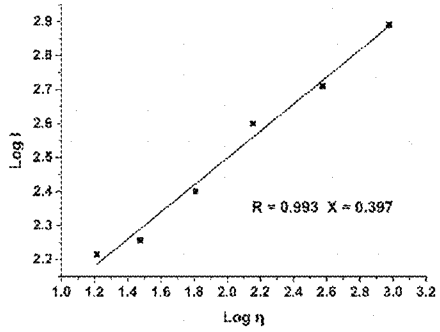
FIG. 4 is a diagram showing the linear relationship between viscosity conditions and fluorescence intensity of the molecular rotor III-4 ($1\times10^{-5}$ M)
Figure 5:
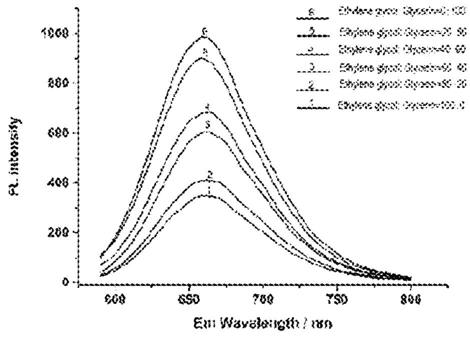
FIG. 5 is a diagram showing the fluorescence emission intensity at different viscosity conditions of the molecular rotor III-28 ($1\times10^{-5}$ M)
Figure 6:
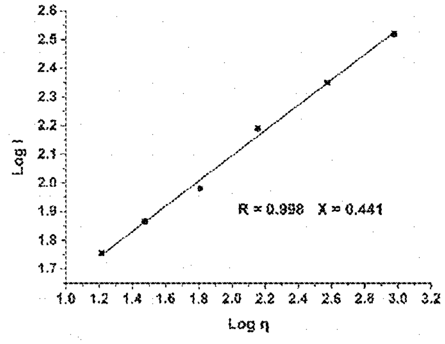
FIG. 6 is a diagram showing the linear relationship between viscosity conditions and fluorescence intensity of the molecular rotor III-28 ($1\times10^{-5}$ M)
Figure 7:
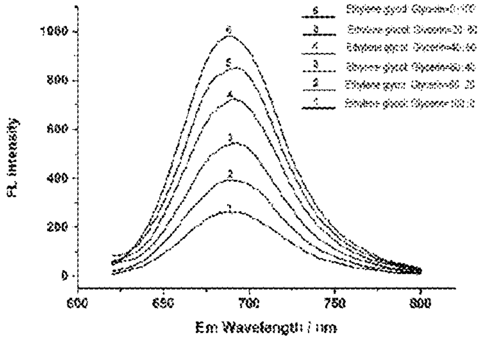
FIG. 7 is a diagram showing the fluorescence emission intensity at different viscosity conditions of the molecular rotor III-34 ($1\times10^{-5}$ M)
Figure 8:
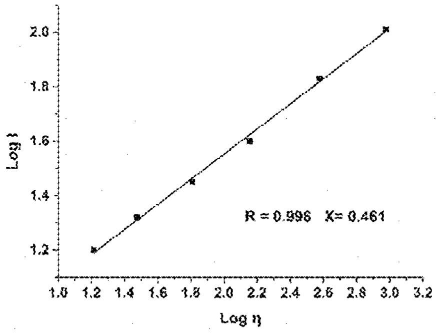
FIG. 8 is a diagram showing the linear relationship between viscosity conditions and fluorescence intensity of the molecular rotor III-34 ($1\times10^{-5}$ M)

Add molecular rotors III-3, III-4, III-28 and III-34 to a diethanol-glycerol mixed solution to prepare a solution with a final concentration of $1\times10^{-5}$ M, conduct excitation at 480 nm, and the fluorescence emission spectra at different viscosity conditions are shown as FIGS. 1, 3, 5 and 7, wherein molecular rotors of the same concentration have gradually increasing fluorescence intensity at different viscosity conditions, which indicates that the fluorescence intensity of molecular rotors increases following the increasing fluorescence of environmental viscosity, and that the relationship between the fluorescence intensity log and the solvent intensity log satisfies the Huffman equation and has a fine linear relation as shown in FIGS. 2, 4, 6, 8, proving that that molecular rotors are sensitive to viscosity and can be used for viscosity tests of unknown samples.

Test Example 3

Figure 9:
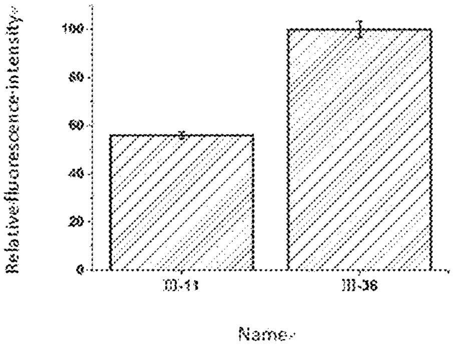
FIG. 9 is a diagram showing the fluorescence background contrast of molecular rotors III-11 and III-36 ($1\times10^{-6}$ M) in PBS.
Figure 10:
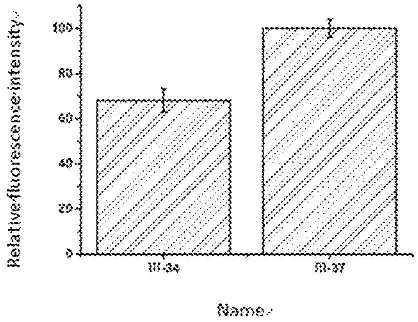
FIG. 10 is a diagram showing the fluorescence background contrast of molecular rotors III-34 and III-37 ($1\times10^{-6}$ M) in PBS.
Figure 11:
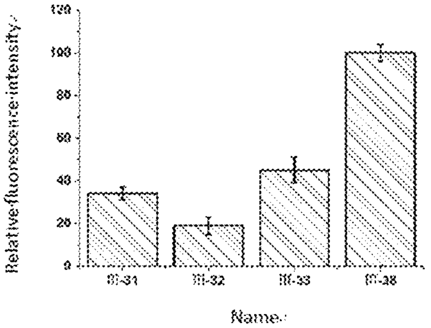
FIG. 11 is a diagram showing the fluorescence background contrast of molecular rotors III-31, III-32, III-33 and III-38 ($1\times10^{-6}$ M) in PBS.
Figure 12:
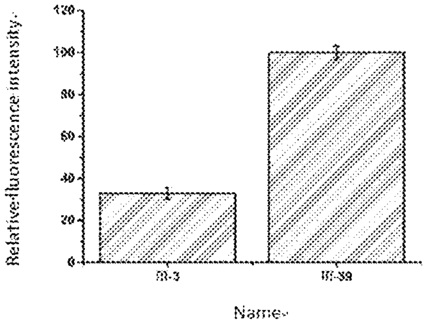
FIG. 12 is a diagram showing the fluorescence background contrast of molecular rotors III-3 and III-39 ($1\times10^{-6}$ M) in PBS.

Add molecular rotors III-11 and III-36; III-34 and III-37; III-31, III-32, III-33 and III-38; III-3 and III-39; III-21 and III-40; III-28, III-29, III-30 and III-41; III-3 and III-42; III-3 and III-43 to a PBS solution to prepare a solution with a final concentration of $1\times10^{-6}$ M, conduct excitation respectively at the maximum excitation of each compound so as to detect their fluorescence intensities in PBS, and normalize each sample with the strongest fluorescence in each group as 100, as shown respectively in FIG. 9, FIG. 10, FIG. 11, FIG. 12, FIG. 13, FIG. 14, FIG. 15 and FIG. 16. According to the results, compared with the molecular rotors with sulfonic acid group substitution and the rotors without substitution on the aromatic ring of the electron withdrawing group, the molecular rotors with cyano group, ester group, sulfoxide, sulphone, sulfonamido substitutions on the aromatic ring of the electron withdrawing group in the present application have lower background fluorescence.

Test Example 4

Compounds III-3, III-4, III-6, III-7, III-8, III-18, III-21 and RNA aptamer (Sequence 10: F30-8Pepper-5 RNA aptamer sequence UUGCCAUGUGUAUGUGG- GUUCGCCCACAUACUCUGAUGAUCCCCAAUC GUGGCGUGUCGGCCUCUCCCAAUCGUGGCGUGU- CGGCCUCUCCCAAUCG UGGCGUGUCGGCCU- CUCCCAAUCGUGGCGUGUCGGCCUCUCC- CAAUCGU GGCGUGUCGGCCUCUCCCAAU- CGUGGCGUGUCGGCCUCUCCCAAUCGUG GCGU- GUCGGCCUCUCCCAAUCGUGGCGUGUCGGCCU- CUCUUCGGAGAGG CACUGGCGCCGGAGAGGCA- CUGGCGCCGGAGAGGCACUGGCGCCGGAGA GGCACUGGCGCCGGAGAGGCACUGGCGCCG- GAGAGGCACUGGCGCCGGA GAGGCACUGGCG- CCGGAGAGGCACUGGCGCCGGGAUCAUUCAUG- GCAA) are specifically bound, and the compound fluorescence after binding is noticeably activated and emits bright fluorescence when being excited by excitation light with an appropriate wavelength, see Table 2 for the optical properties after binding; the compounds can also bind to this aptamer in cells, and cells transcribing the RNA aptamer have bright fluorescence, as shown in FIG. 17A, and cells not expressing the RNA aptamer has no fluorescence, as shown in FIG. 17B, indicating that dyes of this series can be used for nucleic acid labeling.

TABLE 2

| Name | Ex/nm | Em/nm | ε ($M^{-1}$ $cm^{-1}$) | QY (–) | Activation Multiple | $K_d$ (nM) |
|---|---|---|---|---|---|---|
| III-7 | 443 | 485 | 49100 | 0.42 | 691 | 8.0 |
| III-6 | 435 | 497 | 54700 | 0.57 | 16601 | 6.7 |
| III-8 | 458 | 508 | 42500 | 0.30 | 9091 | 27.0 |
| III-4 | 458 | 514 | 44100 | 0.45 | 4748 | 12.0 |
| III-3 | 485 | 530 | 65300 | 0.66 | 3595 | 3.5 |
| III-18 | 515 | 599 | 54400 | 0.43 | 708 | 18.0 |
| III-21 | 577 | 620 | 10000 | 0.58 | 12600 | 6.1 |

Note:
the fluorescence quantum yield was measured by the relative method with Rhodamine 6G as the standard (QY = 0.94).

Test Example 5

A stable cell line (293T/17 cell line) was constructed by fusing the skeleton protein mRNA with the aptamer (ACTB-4Pepper RNA aptamer sequence AUG- GAUGAUGAUAUCGCCGCGCUCGUCGUCGACA- ACGGCUCCGGCAUG UGCAAGGCCGGCUUCG- CGGGCGACGAUGCCCCCCGGGCCGUCUUCCCCU CCAUCGUGGGGCGCCCCAGGCACCAGGGCGUGA- UGGUGGGCAUGGGUC AGAAGGAUUCCUAU- GUGGGCGACGAGGCCCAGAGCAAGAGAGG- CAUCC UCACCCUGAAGUACCCCAUCGAGCACGG- CAUCGUCACCAACUGGGACGA CAUGGAGAA- AAUCUGGCACCACACCUUCUACAAUGAGC- UGCGUGUGGC UCCCGAGGAGCACCCCGUGCU- GCUGACCGAGGCCCCCCUGAACCCCAAG GCCAA- CCGCGAGAAGAUGACCCAGAUCAUGUUUGAGAC- CUUCAACACCC CAGCCAUGUACGUUGCUAUCC- AGGCUGUGCUAUCCCUGUACGCCUCUGG CCGU- ACCACUGGCAUCGUGAUGGACUCCGGUGACGGG- GUCACCCACACU GUGCCCAUCUACGAGGG- GUAUGCCCUCCCCCAUGCCAUCCUGCGUCUGG ACCUGGCUGGCCGGGACCUGACUGACUACCU- CAUGAAGAUCCUCACCGA GCGCGGCUACAGCUU- CACCACCACGGCCGAGCGGGAAAUCGUGCGUGAC AUUAAGGAGAAGCUGUGCUACGUCGCCCUGGAC- UUCGAGCAAGAGAUG GCCACGGCUGCUUCCAG- CUCCUCCCUGGAGAAGAGCUACGAGCUGCCUG ACGGCCAGGUCAUCACCAUUGGCAAUGAGCG- GUUCCGCUGCCCUGAGGC ACUCUUCCAGCCUUC- CUUCCUGGGCAUGGAGUCCUGUGGCAUCCACGAA ACUACCUUCAACUCCAUCAUGAAGUGUGACGU- GGACAUCCGCAAAGACC UGUACGCCAACAC- AGUGCUGUCUGGCGGCACCACCAUGUACCCUGG- CAU UGCCGACAGGAUGCAGAAGGAGAUCACUG-CCCUGGCACCCAGCACAAUG AAGAUCAAGAU-CAUUGCUCCUCCUGAGCGCAAGUACUCCGUGUG-GAUC GGCGGCUCCAUCCUGGCCUCGCUGUCCAC-CUUCCAGCAGAUGUGGAUCA GCAAGCAGGAG-UAUGACGAGUCCGGCCCCUCCAUCGUCCACCGC-AAAUG CUUCUAGCACUCGCUAGAGCAUGGUUAA-GCUUCCCACGGAGGAUCCCCA AUCGUGGCGUGU-CGGCCUCUCCCAAUCGUGGCGUGUCGGCCU-CUCCCAA UCGUGGCGUGUCGGCCUCUCCCAAUC-GUGGCGUGUCGGCCUCUCCCAAU CGUGGCGUGU-CGGCCUCUCUUCGGAGAGGCACUGGCGCCG-GAGAGGCAC UGGCGCCGGAGAGGCACUGGCGCC-GGAGAGGCACUGGCGCCGGGAUCCU CCGUGGG), and, under the conditions of conventional mammalian cell culture (37° C., 5% carbon dioxide, 100% relative humidity), the cells were digested after the cell line and control cells (293T/17) grew to a cell confluence of 90%, and were centrifuged at 800 rpm, and then the cells were re-suspended with PBS containing 0.2 μM of III-3 and 0.2 μM of III-43 molecules, and were incubated for 5 minutes before flow detection, see FIGS. 18A and 18B for the detection results; the III-3 molecular rotors could specifically mark the mRNA of skeleton protein in cell lines expressing target RNA, and there was no obvious background fluorescence (as shown in FIG. 18A), while the background fluorescence of III-43 molecules was higher than III-3, and it was unclear whether ACTB was expressed (see FIG. 18B).

The invention claimed is:

1. A fluorescent dye, the structural formula of which is shown as Formula (I), (I)

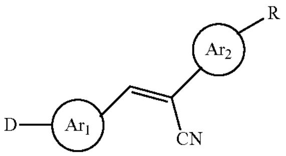

wherein:

D- is HO— or $N(X_1)(X_2)$—, $X_1$ and $X_2$ are respectively and independently selected from hydrogen, alkyl and modified alkyl; and $X_1$ and $X_2$ are optionally interconnected, and form a lipid heterocyclic ring with N atoms;

R is selected from cyano group, carboxy, amide group, ester group, sulfoxide group, sulphone group, sulfonic ester group or sulfonamido group;

$Ar_1$ is selected from the following Formulae (II-2) to (II-22) and $Ar_2$ is selected from the following Formulae (II-1) to (II-4):

(II-1)

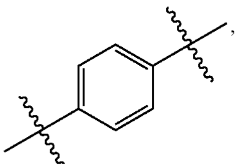

(II-2)

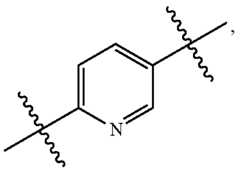

-continued (II-3)

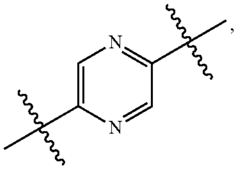

(II-4)

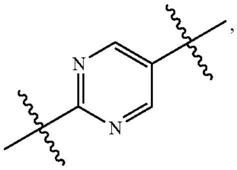

(II-5)

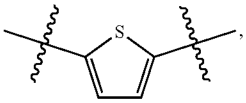

(II-6)

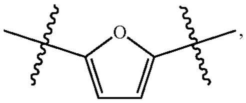

(II-7)

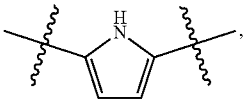

(II-8)

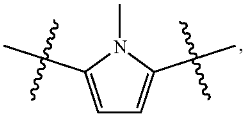

(II-9)

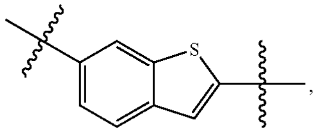

-continued (II-10)

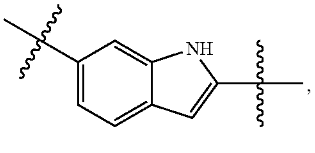

(II-11)

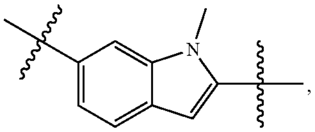

(II-12)

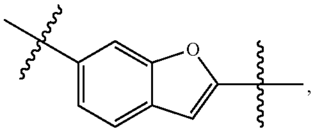

(II-13)

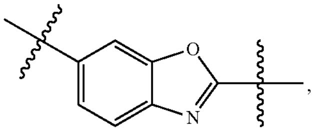

(II-14)

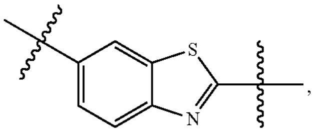

(II-15)

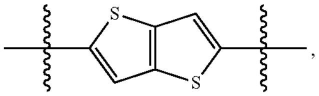

(II-16)

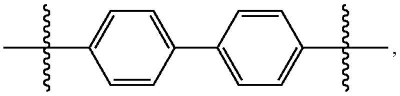

(II-17)

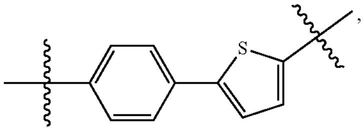

(II-18)

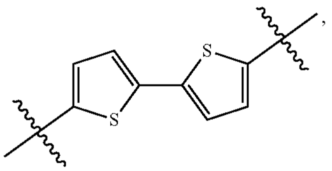

(II-19)

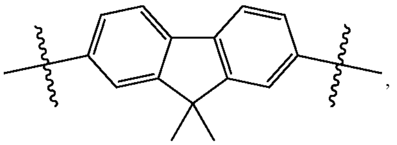

(II-20)

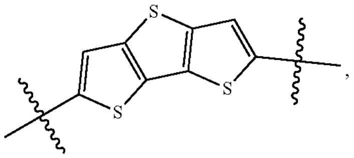

-continued (II-21)

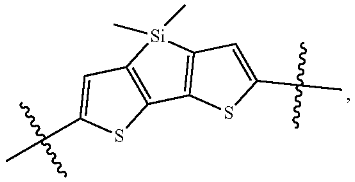

(II-22)

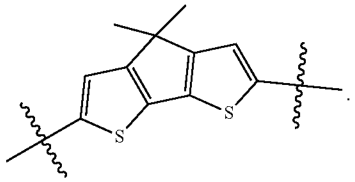

wherein hydrogen atoms in $Ar_1$ and $Ar_2$ being optionally, respectively and independently substituted by halogen atoms, hydroxyl group, aldehyde group, carboxyl group, ester group, amide group, cyano group, sulfonic acid group, phosphoric acid group, amino group, primary amino group, secondary amino group, alkyl or modified alkyl;

$X_1$ and $X_2$ optionally and independently form a lipid heterocyclic ring with $Ar_1$;

wherein: the "alkyl" is respectively and independently $C_1$-$C_{10}$ straight or branched alkyl; optionally, the "alkyl group" is $C_1$-$C_7$, straight or branched alkyl: optionally, the "alkyl group" is $C_1$-$C_5$ straight or branched alkyl; optionally, the "alkyl group" is selected from methyl, ethyl, n-propyl, isopropyl, n-butyl, isobutyl, tertiary butyl, sec-butyl, n-amyl, 1-methyl butyl, 2-methyl butyl, 3-methyl butyl, isoamyl, 1-ethyl propyl, neoamyl, n-hexyl, 1-methyl amyl, 2-methyl amyl, 3-methyl amyl, isohexyl, 1,1-dimethyl butyl, 2,2-dimethyl butyl, 3,3-dimethyl butyl, 1,2-dimethyl butyl, 1,3-dimethyl butyl, 2,3-dimethyl butyl, 2-ethyl butyl, n-heptyl, 2-methyl hexyl, 3-methyl hexyl, 2,2-dimethyl amyl, 3,3 dimethyl amyl, 2,3-dimethyl amyl, 2,4-dimethyl amyl, 3-ethyl amyl or 2,2,3-methyl butyl;

the "modified alkyl" is respectively and independently a group obtained by replacing any carbon atom in alkyl with one or more groups of halogen atom, —OH, —CO—, —O—, —CN—, —S—, $—SO_2—$, —(S═O)—, azido, primary amino group, secondary amino group, tertiary amino group, and quaternary ammonium base, and the modified alkyl has 1-10 carbon atoms, wherein the carbon-carbon single bond is optionally and independently replaced by a carbon-carbon double bond or a carbon-carbon triple bond;

the replacement of carbon atoms refers to that carbon atoms or the carbon atoms and hydrogen atoms thereon together are replaced by a corresponding group;

the "halogen atom" is respectively and independently F, Cl, Br or I;

the "lipid heterocyclic ring" is a saturated or unsaturated 4- to 15-membered monocyclic or polycyclic lipid heterocyclic ring containing one or more heteroatoms of N, O, S, or Si on the ring, and the lipid heterocyclic ring is —S—, —SO— or $—SO_2—$ when there are S atoms on the ring; the lipid heterocyclic ring is optionally substituted by a halogen atom, an alkyl, an aryl or a modified alkyl;

the "arylene" is a 5- to 13-membered monocyclic or dicyclic or fused dicyclic or fused polycyclic subaromatic group;

the "sub-heteroaryl" is a 5- to 13-membered monocyclic or dicyclic or fused dicyclic or fused polycyclic subheteroaromatic group containing one or more heteroatoms of N, O, S, or Si on the ring;

the "ester group" is R'(C═O)OR" group;

the "amide group" is R'CONR"R'" group;

the "sulfonic acid group" is $R'SO_3H$ group;

the "sulfonic ester group" is $R'SO_2OR"$ group;

the "sulfonamido group" is $R'SO_2NR"R'"$ group;

the "phosphoric acid group" is $R'OP(═O)(OH)_2$ group;

the "sulphone group" is $R'SO_2R"$ group;

the "sulfoxide group" is R'SOR" group;

the "primary amino group" is $R'NH_2$ group;

the "secondary amino group" is R'NHR" group;

the "tertiary amino group" is R'NR"R'" group;

the "quaternary ammonium base" is $R'R"R'"R""N^+$ group;

each R', R", R'", R"" respectively and independently being single bond, hydrogen, alkyl, alkylene, modified alkyl or modified alkylene;

the "alkylene" is $C_1$-$C_{10}$ straight or branched alkylene; optionally, it is $C_1$-$C_7$ straight or branched alkylene: optionally, it is $C_1$-$C_5$ straight or branched alkylene; and the "modified alkylene" is a group obtained by replacing any carbon atom in $C_1$-$C_{10}$ (preferably $C_1$-$C_6$) alkylene with a group selected from —O—, —OH, —CO—, —CS—, and —(S═O)—.

2. The fluorescent dye according to claim 1, wherein the "modified alkylene" is a group containing one or more groups selected from —OH, —O—, ethylene glycol unit, monosaccharide unit, —O—CO—, —NH—CO—, $—SO_2—O—$, —SO—, $Me_2N—$, $Et_2N—$, —S—S—, —CH═CH—, F, Cl, Br, I, and cyano group.

3. The fluorescent dye according to claim 1, wherein the compound represented by Formula (I) is selected from the compounds below:

III-4

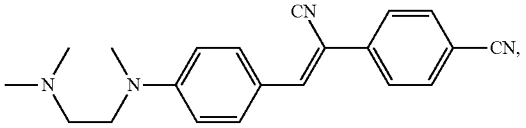

III-5

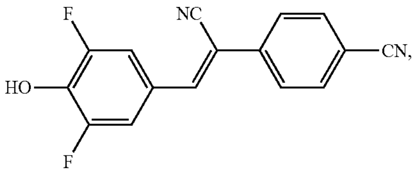

III-6

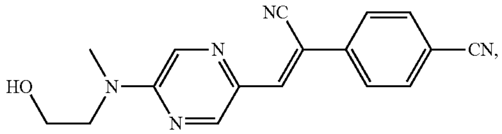

III-7

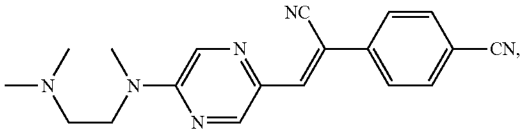

-continued

III-8

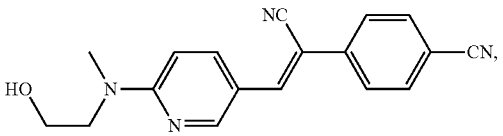

III-9

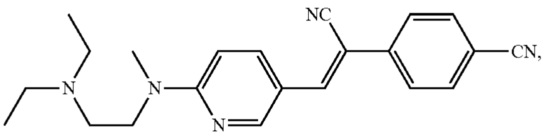

III-10

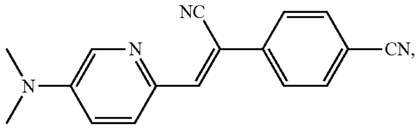

III-11

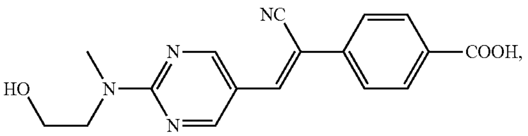

III-12

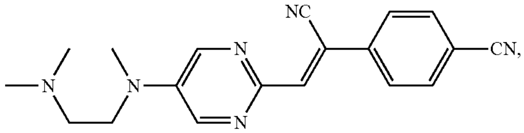

III-13

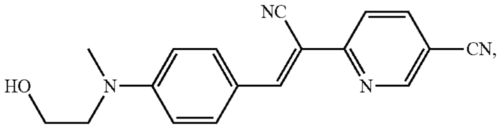

III-14

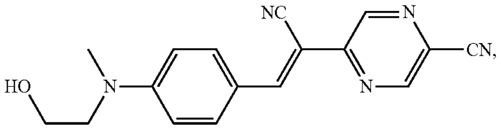

III-16

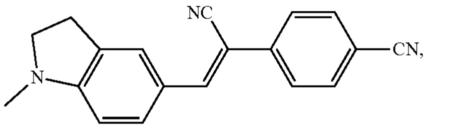

III-17

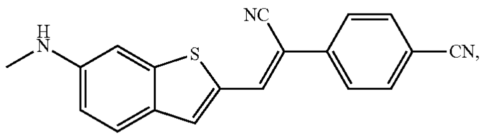

III-18

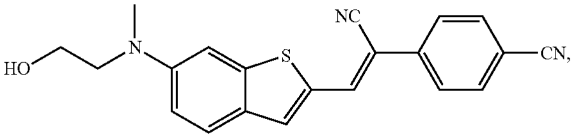

-continued
III-19
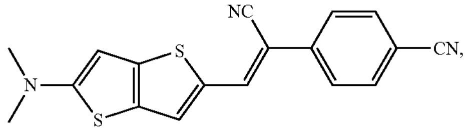
III-20
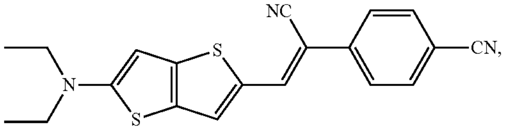
III-21
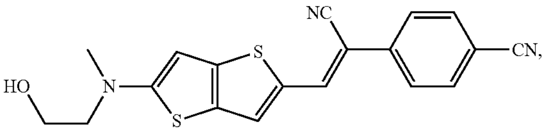
III-22
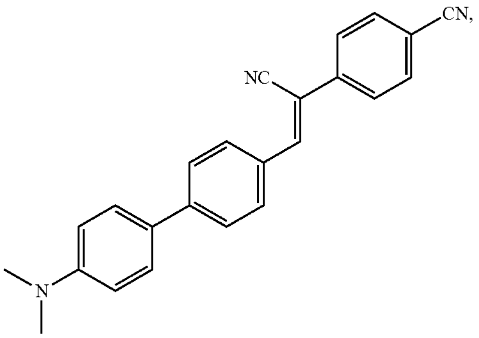
III-23
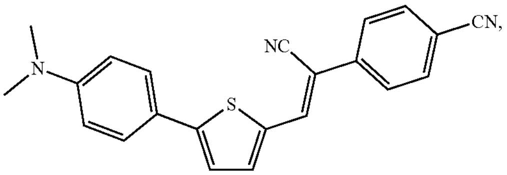
III-24
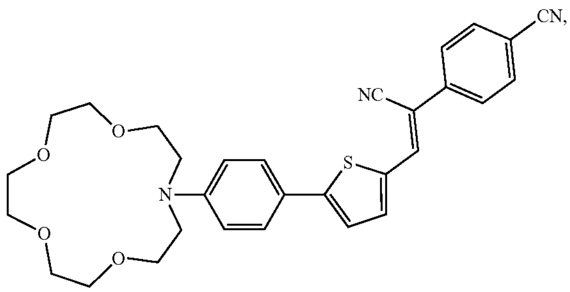
III-25
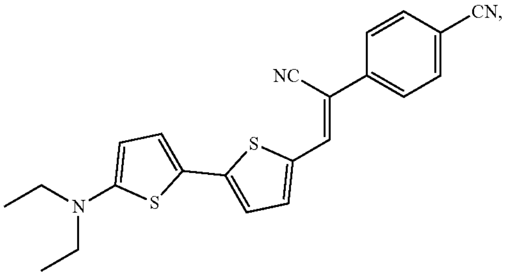
-continued
III-26
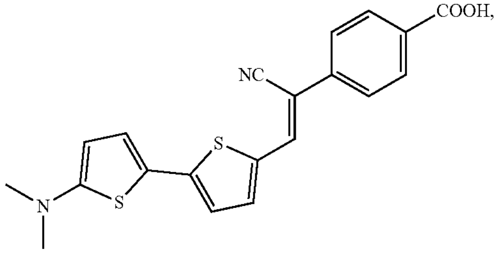
III-27
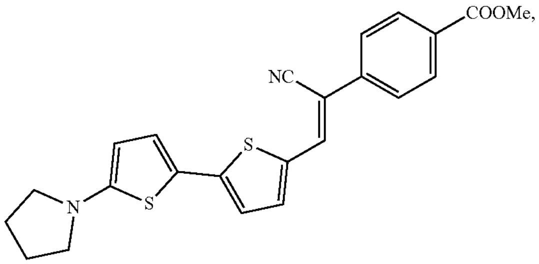
III-28
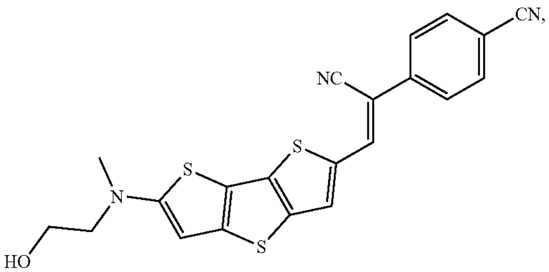
III-29
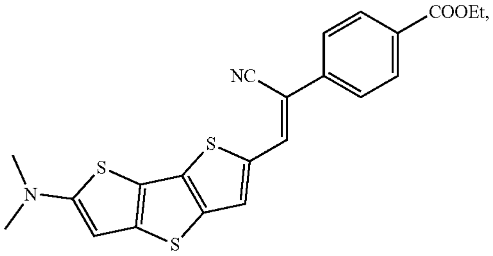
III-30
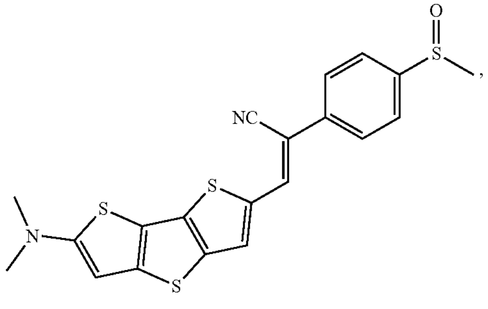

-continued
III-31
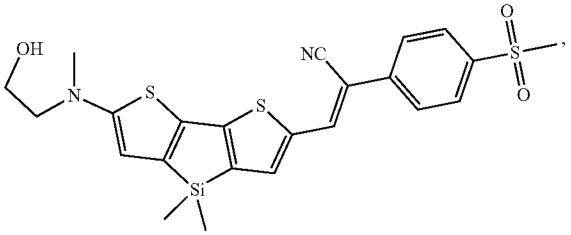
III-32
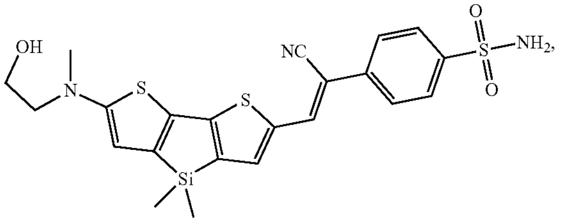
III-33
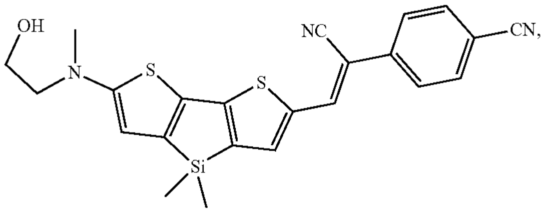
-continued
III-34
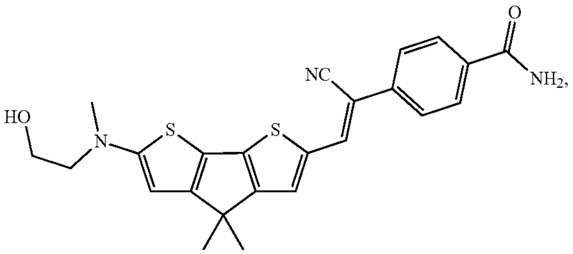
III-35
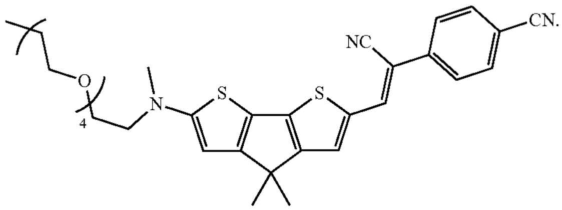
4. A method of preparing the fluorescent dye according to claim 1, including a step of aldol condensation reaction between a compound of Formula (a) and a compound of Formula (b),
(a)
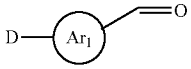
(b)
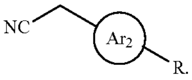
5. A fluorescent activated and lighted probe solution, comprising the fluorescent dye according to claim 1.
* * * * *

SEQUENCE LISTING

```
<160> NUMBER OF SEQ ID NOS: 2

<210> SEQ ID NO 1
<211> LENGTH: 390
<212> TYPE: RNA
<213> ORGANISM: Artificial Sequence
<220> FEATURE:
<223> OTHER INFORMATION: Synthesized

<400> SEQUENCE: 1

uugccaugug uaugugggguu cgcccacaua cucugaugau ccccaaucgu ggcgugucgg      60

ccucucccaa ucguggcgug ucggccucuc ccaaucgugg cgugucggcc ucucccaauc     120

guggcguguc ggccucuccc aaucguggcg ugucggccuc ucccaaucgu ggcgugucgg     180

ccucucccaa ucguggcgug ucggccucuc ccaaucgugg cgugucggcc ucucuucgga     240

gaggcacugg cgccggagag gcacuggcgc cggagaggca cuggcgccgg agaggcacug     300

gcgccggaga ggcacuggcg ccggagaggc acuggcgccg gagaggcacu ggcgccggag     360

aggcacuggc gccgggauca uucauggcaa                                      390

<210> SEQ ID NO 2
<211> LENGTH: 1373
<212> TYPE: RNA
<213> ORGANISM: Artificial Sequence
<220> FEATURE:
<223> OTHER INFORMATION: Synthesized

<400> SEQUENCE: 2

auggaugaug auaucgccgc gcucgucguc gacaacggcu ccggcaugug caaggccggc      60

uucgcgggcg acgaugcccc ccgggccguc uuccccucca ucguggggcg ccccaggcac     120

cagggcguga uggugggcau gggucagaag gauuccuaug ugggcgacga ggcccagagc     180

aagagaggca uccucacccu gaaguacccc aucgagcacg gcaucgucac caacugggac     240

gacauggaga aaaucuggca ccacaccuuc uacaaugagc ugcgugugggc ucccgaggag     300

cacccccgugc ugcugaccga ggcccccug aaccccaagg ccaaccgcga gaagaugacc     360

cagaucaugu uugagaccuu caacaccccca gccauguacg uugcuaucca ggcugugcua     420

ucccuguacg ccucuggccg uaccacuggc aucgugaugg acuccggguga cggggucacc     480

cacacugugc ccaucuacga gggguaugcc cucccccaug ccauccugcg ucuggaccug     540

gcuggccggg accugacuga cuaccucaug aagauccuca ccgagcgcgg cuacagcuuc     600

accaccacgg ccgagcggga aaucgugcgu gacauuaagg agaagcugug cuacgucgcc     660
```

-continued

| | | | | | | |
|---|---|---|---|---|---|---|
| cuggacuucg | agcaagagau | ggccacggcu | gcuuccagcu | ccucccugga | gaagagcuac | 720 |
| gagcugccug | acggccaggu | caucaccauu | ggcaaugagc | gguuccgcug | cccugaggca | 780 |
| cucuuccagc | cuuccuuccu | gggcauggag | uccuguggca | uccacgaaac | uaccuucaac | 840 |
| uccaucauga | agugugacgu | ggacauccgc | aaagaccugu | acgccaacac | agugcugucu | 900 |
| ggcggcacca | ccauguaccc | uggcauugcc | gacaggaugc | agaaggagau | cacugcccug | 960 |
| gcacccagca | caaugaagau | caagaucauu | gcuccuccug | agcgcaagua | cuccgugugg | 1020 |
| aucggcggcu | ccauccuggc | cucgcugucc | accuuccagc | agauguggau | cagcaagcag | 1080 |
| gaguaugacg | aguccggccc | cuccaucguc | caccgcaaau | gcuucuagca | cucgcuagag | 1140 |
| caugguuaag | cuucccacgg | aggaucccca | aucguggcgu | gucggccucu | cccaaucgug | 1200 |
| gcgugucggc | cucucccaau | cguggcgugu | cggccucucc | caaucguggc | gugucggccu | 1260 |
| cucccaaucg | uggcgugucg | gccucucuuc | ggagaggcac | uggcgccgga | gaggcacugg | 1320 |
| cgccggagag | gcacuggcgc | cggagaggca | cuggcgccgg | gauccuccgu | ggg | 1373 |